(12) United States Patent
Kasiutsich et al.

(10) Patent No.: US 9,766,124 B2
(45) Date of Patent: Sep. 19, 2017

(54) ATTACHMENT AND ALIGNMENT DEVICE FOR OPTICAL SOURCES, DETECTORS AND ANALYSERS, AND MODULAR ANALYSIS SYSTEM

(71) Applicant: Servomex Group Limited, Crowborough, East Sussex (GB)

(72) Inventors: Vasili Kasiutsich, Crowborough (GB); Martin Lopez, Rotherfield (GB)

(73) Assignee: Servomex Group Limited, East Sussex (GB)

( * ) Notice: Subject to any disclaimer, the term of this patent is extended or adjusted under 35 U.S.C. 154(b) by 57 days.

(21) Appl. No.: 14/673,941

(22) Filed: Mar. 31, 2015

(65) Prior Publication Data
US 2015/0285679 A1 Oct. 8, 2015

(30) Foreign Application Priority Data

Apr. 4, 2014 (GB) .................................. 1406152.7

(51) Int. Cl.
*G01J 3/02* (2006.01)
*G02B 27/10* (2006.01)
(Continued)

(52) U.S. Cl.
CPC .......... *G01J 3/0237* (2013.01); *G01J 3/0291* (2013.01); *G01J 3/42* (2013.01); *G01N 21/3504* (2013.01);
(Continued)

(58) Field of Classification Search
CPC . G01J 3/0237; G01N 21/39; G01N 2012/399; G01N 2201/0621; G01N 2201/068; G02B 27/1006
See application file for complete search history.

(56) References Cited

U.S. PATENT DOCUMENTS 3,573,470 A * 4/1971 Haley ................ G01N 21/05
250/239
3,861,802 A * 1/1975 Belmear, Jr. ......... G01N 21/534
250/573
(Continued)

FOREIGN PATENT DOCUMENTS

CN 201081762 2/2008
EP 2 530 452 A1 12/2012
(Continued)

OTHER PUBLICATIONS

Combined Search and Examination Report dated Sep. 29, 2015 for GB Application No. GB1505533.8; 8 pages.
(Continued)

*Primary Examiner* — Sang Nguyen
(74) *Attorney, Agent, or Firm* — Daly, Crowley, Mofford & Durkee LLP

(57) ABSTRACT

A device is provided for combining two or more separate components of an optical analysis system, to use common entrance and exit apertures for optical measurements across a measurement space such as a stack, combustion chamber, duct or pipeline, in such way that the optical paths from the respective light sources to detectors are substantially the same, enabling multiple optical measurements over a single optical path or closely aligned optical paths with equivalent ambient conditions such as temperature and pressure distribution and background substance concentrations. The device and a set of interconnectable devices forming a modular system are useful, for example, in absorption spectroscopy, such as for measuring the amount fraction of the chemical constituents of a fluid in a measurement volume.

31 Claims, 18 Drawing Sheets

(51) Int. Cl.
*G01N 21/29* (2006.01)
*G01N 21/39* (2006.01)
*G01N 21/3504* (2014.01)
*G01J 3/42* (2006.01)

(52) U.S. Cl.
CPC ......... *G01N 21/39* (2013.01); *G02B 27/1006* (2013.01); *G01N 2021/399* (2013.01); *G01N 2201/024* (2013.01); *G01N 2201/068* (2013.01); *G01N 2201/0612* (2013.01)

(56) References Cited

U.S. PATENT DOCUMENTS

| | | | | |
|---|---|---|---|---|
| 3,972,627 | A * | 8/1976 | Rabl | G01N 21/272 250/428 |
| 4,250,394 | A * | 2/1981 | O'Connor | G01N 33/54313 250/574 |
| 5,331,409 | A | 7/1994 | Thurtell et al. | |
| 5,401,966 | A * | 3/1995 | Gray | A61B 5/0836 250/339.13 |
| 5,734,468 | A * | 3/1998 | McNeal | B01L 3/021 356/244 |
| 5,773,828 | A | 6/1998 | Akiyama et al. | |
| 5,872,361 | A * | 2/1999 | Paoli | G01N 21/534 250/341.8 |
| 5,905,271 | A * | 5/1999 | Wynn | G01J 3/02 250/573 |
| 6,275,288 | B1 * | 8/2001 | Atkinson | G01N 21/39 250/339.13 |
| 6,414,754 | B1 * | 7/2002 | Johnson | G01N 15/1456 250/222.2 |
| 6,903,818 | B2 * | 6/2005 | Cerni | G01N 15/14 250/341.8 |
| 7,248,755 | B2 | 7/2007 | Sappey et al. | |
| 2002/0158202 | A1 | 10/2002 | Webber et al. | |
| 2011/0150035 | A1 | 6/2011 | Hanson et al. | |
| 2012/0307241 | A1 * | 12/2012 | Maity | G01J 3/02 356/326 |
| 2014/0099659 | A1 * | 4/2014 | Keller | G01N 21/6486 435/29 |

FOREIGN PATENT DOCUMENTS

| | | |
|---|---|---|
| EP | 2 118 638 B1 | 5/2013 |
| JP | H 10115210 A | 6/1998 |
| WO | WO 95/25950 | 9/1995 |
| WO | WO 2009/052157 A1 | 4/2009 |
| WO | WO 2010/081161 A1 | 8/2010 |

OTHER PUBLICATIONS

Response to Combined Search and Examination Report filed Jun. 6, 2016 for GB Application No. GB1505533.8; 95 pages.
Extended European Search Report dated Jul. 9, 2015 for European Application No. 15161624.0; 7 pages.
Response to European Extended Search Report filed Apr. 7, 2016 for European Application No. 15161624.0; 19 pages.
Search Report dated May 20, 2014 for Great Britain Application No. 1406152.7; 6 pages.
Teichert et al.; Simultaneous In Situ Measurement of CO, $H_2O$, and Gas Temperatures in a Full-Sized Coal-Fired Power Plant by Near-Infrared Diode Lasers; Applied Optics, vol. 42, No. 12, Apr. 20, 2003, pp. 2043-2051.
Furlong et al.; Combustion Control Using a Multiplexed Diode-Laser Sensor System; Combustion Symposium, 1996, 25 pages.
Ebert et al.; Simultaneous Diode-Laser Based In Situ Detection of Multiple Species and Temperature in a Gas-Fired Power Plant; Proceedings of the Combustion Institute, vol. 28, 2000, pp. 423-430.
Ebert et al.; Sensitive In Situ Detection of CO and $O_2$ in a Rotary Kiln-Based Hazardous Waste Incinerator Using 760 nm and New 2.3 µm Diode Laser; Proceedings of the Combustion Institute. vol. 30, Jan. 2005, pp. 1611-1615.
Chao et al.; Development of Laser Absorption Techniques for Real-Time, In Situ Dual-Species Monitoring ($NO/NH_3$, $CO/O_2$) in Combustion Exhaust; Proceedings of the Combustion Institute, vol. 34, 2012, pp. 3583-3592.
Brooke et al.; Greenhouse Gas Measurements Over a 144km Open Path in the Canary Islands; Atmos. Meas. Tech, vol. 5, 2012, pp. 2309-2319.
Baer et al.; Muitiplexed diode-laser sensor systems for simultaneous $H_2O$, $O_2$, and temperature measurements; Optics Letters, vol. 19, Issue 22, Nov. 15, 1994, pp. 1900-1902.

* cited by examiner

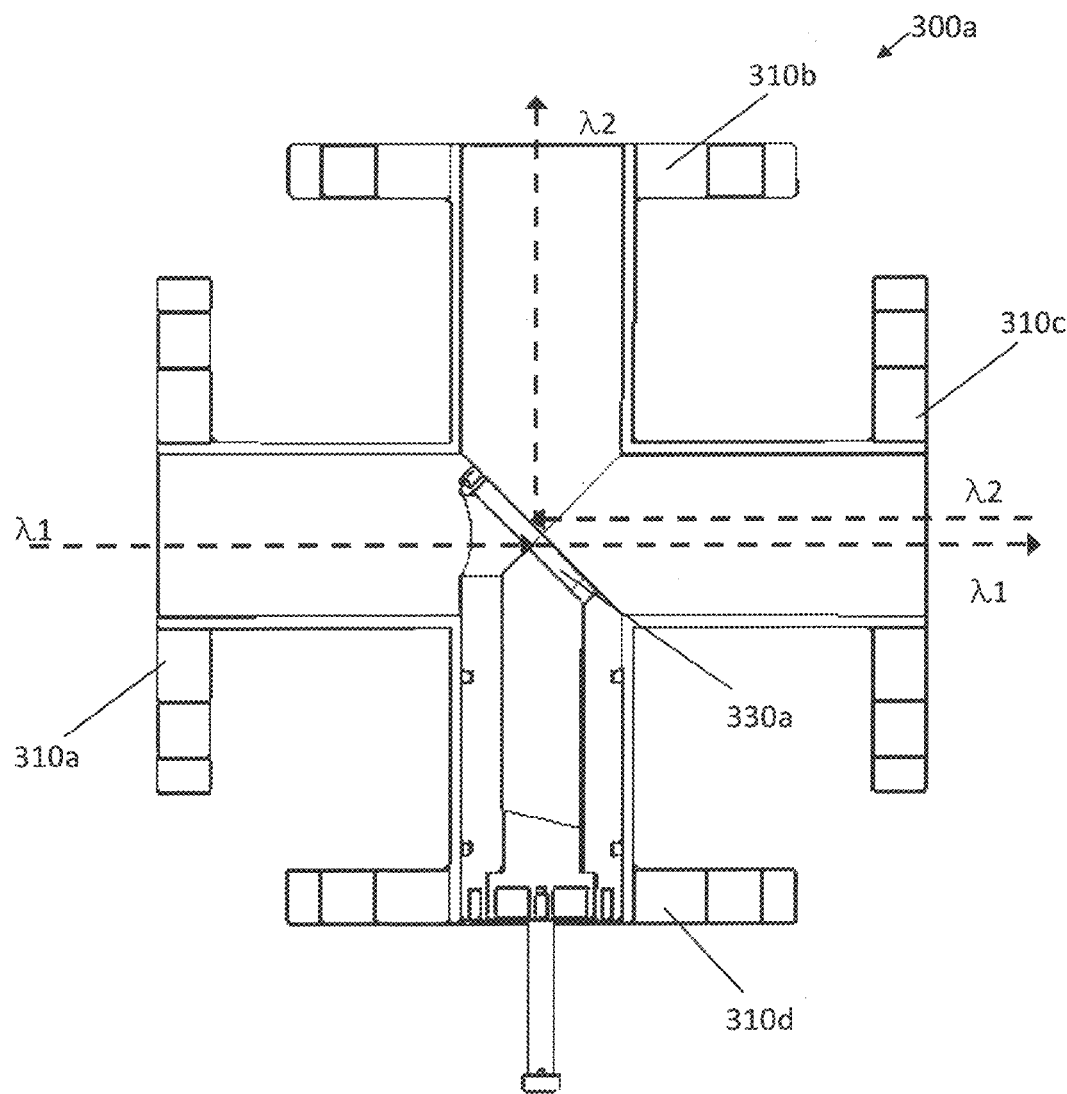

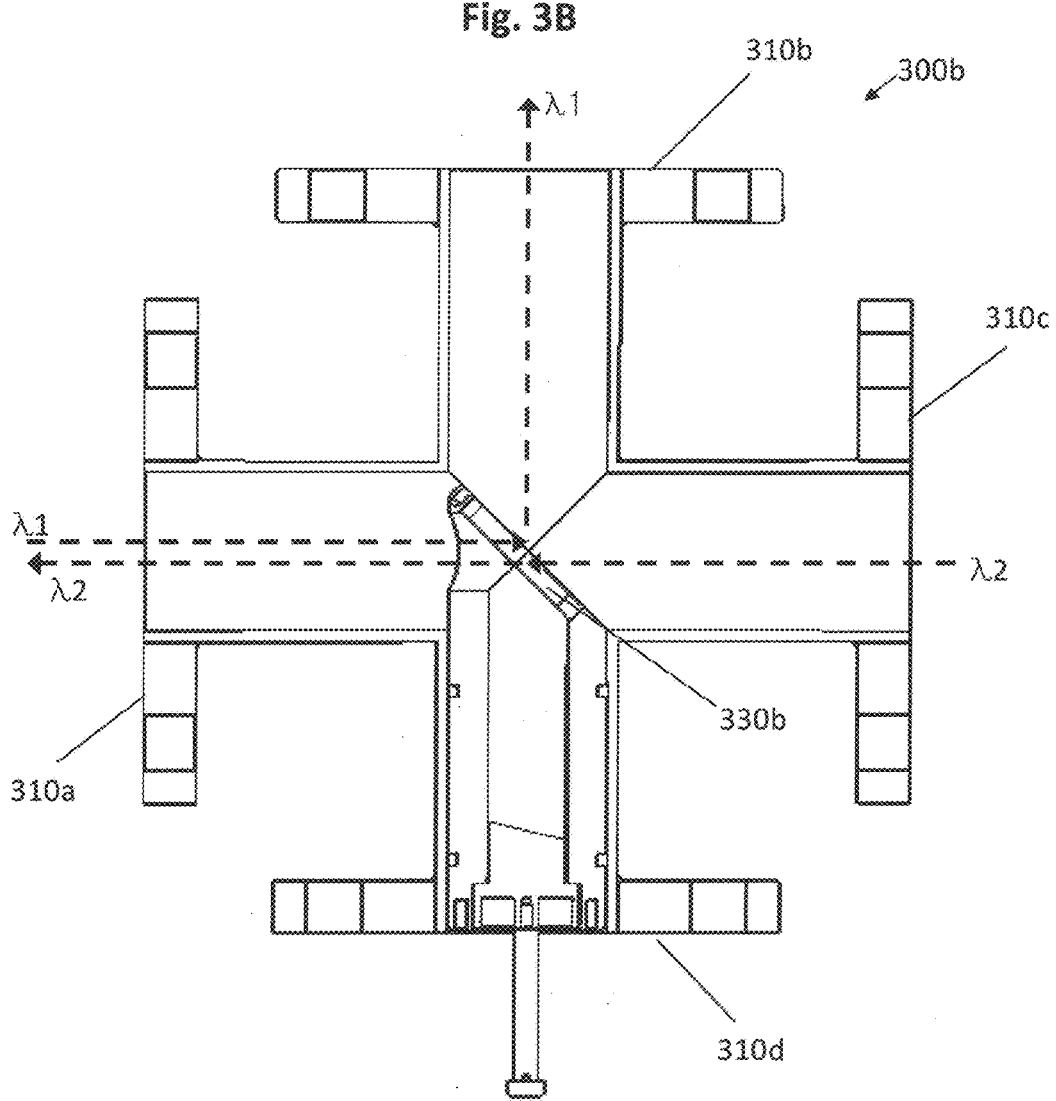

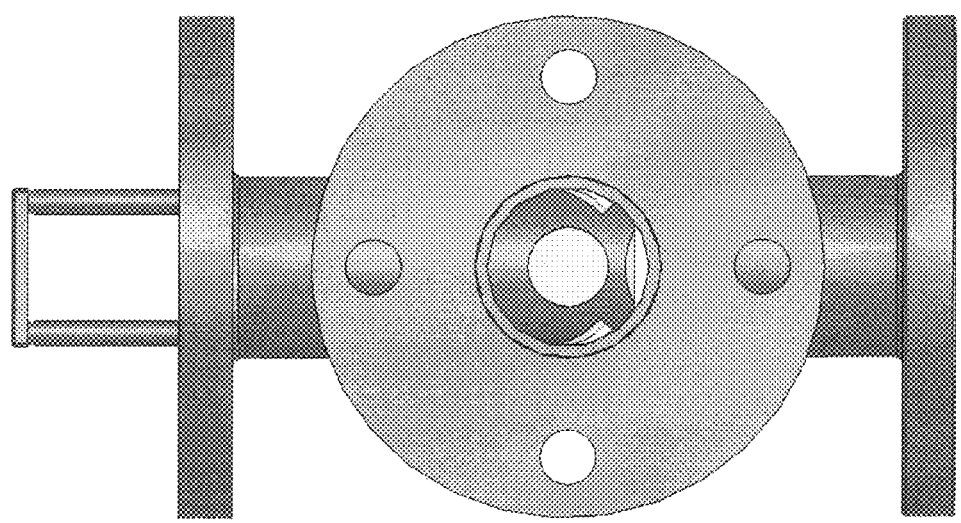
Fig. 4A  300a, 300b

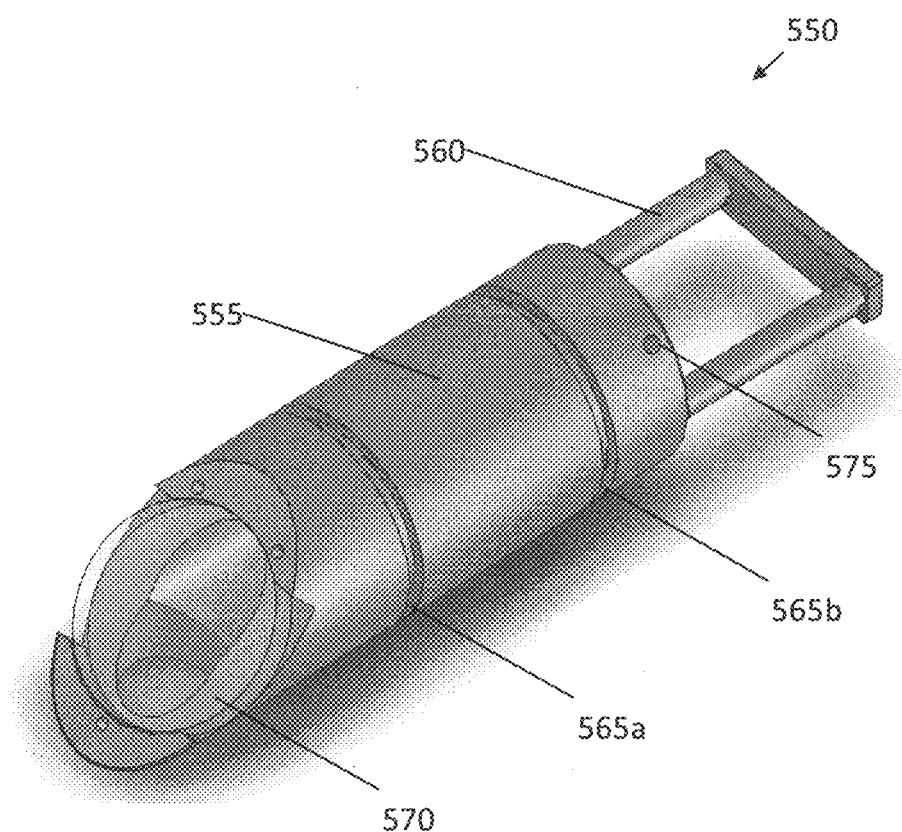

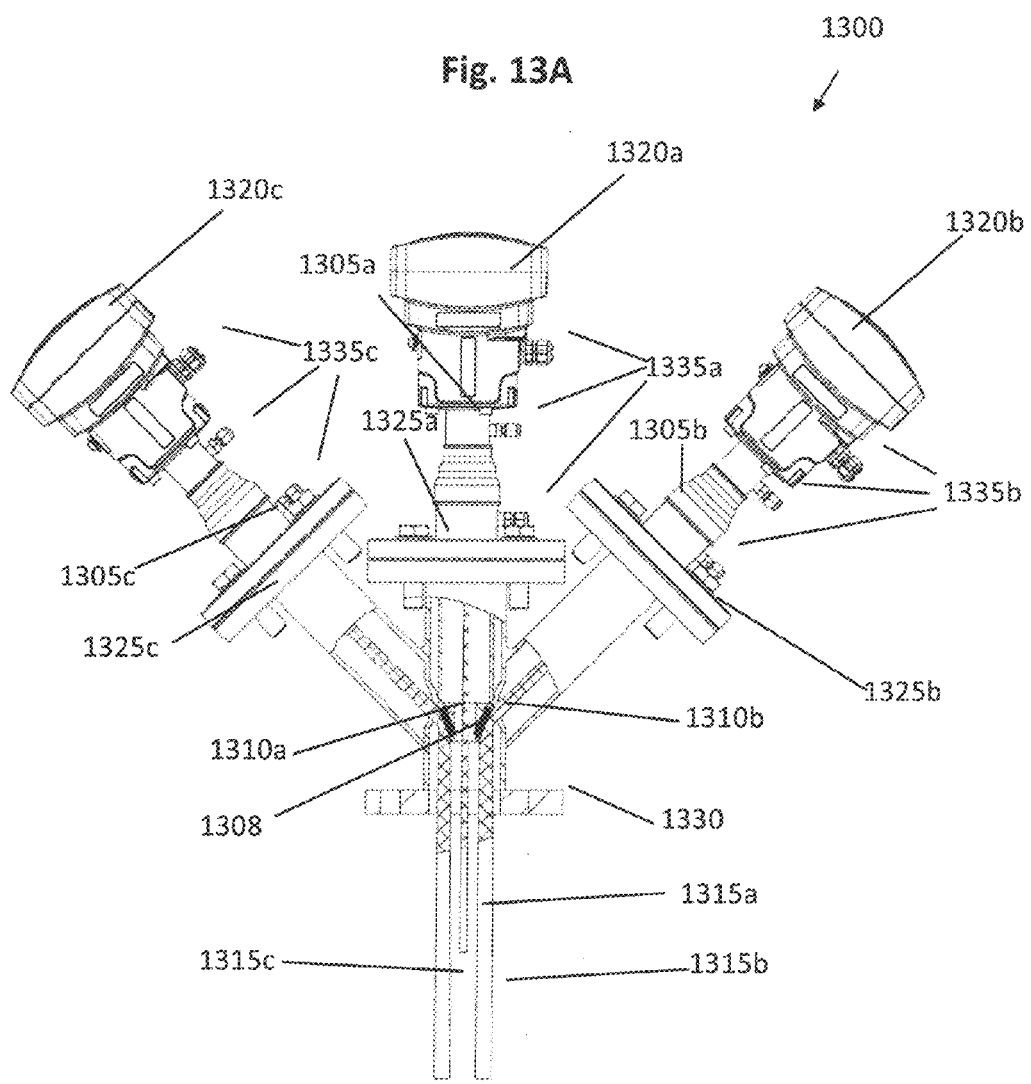

ATTACHMENT AND ALIGNMENT DEVICE FOR OPTICAL SOURCES, DETECTORS AND ANALYSERS, AND MODULAR ANALYSIS SYSTEM

CROSS REFERENCE TO RELATED APPLICATIONS

This application claims priority under 35 U.S.C. §119 TO United Kingdom patent application No. GB 1406152.7 filed on Apr. 4, 2014, which is incorporated herein by reference in its entirety.

FIELD OF THE INVENTION

This invention relates to attachment and alignment devices for optical sources, detectors and analysers, and in particular to attachment and alignment devices that can provide a multi-component analyser system incorporating optical analysers and/or sources and/or detectors that may be used, for example, in absorption spectroscopy measurements.

BACKGROUND

Optical analysers have long been used for the measurement of parameters of interest within a measurement volume, such as the amount fraction measurements of a chemical component or components of interest within a test medium or the measurement volume temperature. The measurement parameter is also referred to as the measurand. The principles of these optical measurements are well established and will not be discussed in detail within this specification. These optical measurements may typically involve measuring how much light at a particular wavelength or across a wavelength range is absorbed by the chemical component of interest along a particular optical path-length. This is known as absorption spectroscopy and is well known to a skilled person. Reflective optics and/or refractive optics may be used to shape and steer the light beam(s).

In absorption spectroscopy, a light source and an optical detector are placed near (for example on opposite sides of) a measurement volume. The light beam path from the source to the detector may be along a single pass straight line, or may involve one or more reflective passes, such as a multi-pass optical cell in order to increase the absorption path length and hence enhance absorption sensitivity. The light source used may be a diode laser, a quantum cascade laser (QCL), an inter-band cascade laser (ICL), an external cavity laser diode, an external cavity QCL, an external cavity ICL, a light emitting diode (LED) or an incandescent (black or grey body radiation) source, or any other suitable light source known in the art. Depending on the incident light intensity and wavelength and the required sensitivity and time response, the optical detectors may be photodiodes, photomultiplier tubes (PMT), photoresistors or thermal devices such as pyroelectric, thermopile or bolometer detectors, or any other suitable detectors known in the art.

The following illustration will be given for a typical tunable diode laser spectroscopy (TDLS) arrangement for gaseous measurement, but similar considerations and issues may be envisioned for the other optical measurement methods described above and for measuring constituents of any test medium. This particular illustrative example relates to a cross stack gas absorption analyser, with the light source mounted on one side of the stack and the photodetector mounted on the other side. Typically, this will be designed for measurement of a single component within the gas mixture and hence there will be a single diode laser source and a single wavelength sensitive photo-detector. Both the source and the photo-detector must be sufficiently aligned with each other to be able to produce a suitable magnitude of light passed through the stack and incident on the photo-detector to allow the required absorption measurement to take place. The light source and the photo-detector are normally mounted within suitable housings to protect them from the environment, which housings may also contain some or all of the associated electronics and software required to power, control and perform the required measurement algorithms. These housings will typically be mounted to the stack via tubes (nozzles) connected to flanges or some other suitable means, which act as physical support mechanisms in a fixed position and also provide a sealed connection between the stack gas and the ambient environment. Typically, these flanges or attachment means will contain some physical adjustment means for optical co-alignment between the source and the detector by moving the whole source and photodetector housings to different angular positions to compensate for mechanical inaccuracies in e.g. mounting of the nozzles, the flanges and the source and detector enclosures on the flanges.

Dependent on the application, one component measurement may be sufficient. However, for certain applications, measurement of several independent or dependent components may be required. For example, in a combustion application, it might be required to monitor the oxygen concentration and the carbon monoxide concentration in order to optimise burn efficiency. Potentially, the fuel concentration may also be measured to check for flame out conditions and so a total of three measurements such as $O_2$, CO and hydrocarbons ($CH_4$ or $C_2H_4$, etc.) would be required. This could be done with two or more independent analysers mounted at separate positions on the stack, either at the same height at different angular positions on the same diameter (see R. M. Spearrin, W. Ren, J. B. Jeffries, R. K. Hanson, Multi-band infrared $CO_2$ absorption sensor for sensitive temperature and species measurements in high-temperature gases, Appl. Phys. B DOI 10.1007/s00340-014-5772-7) or different spatial locations across stack cross-section (see US 2011/0045422 A1 and U.S. Pat. No. 5,813,767) or in the same angular position on the stack, but at different heights (see US 2006/0044562 A1) or finally a combination of all three arrangements. However, mounting all the analysers at different physical locations has a number of disadvantages:

i) The optical beam paths probed by all of the analysers are not equivalent. This means that any dependent parameters do not exactly correlate in either quantity or time. This is especially significant if active feed-back mechanisms are being used, such as to increase or decrease the supply of fuel or oxygen (air) in combustion applications to maintain combustion efficiency at an optimal level. Any lack of correlation or synchronisation could lead to adjustment errors and potentially oscillatory effects, where the feedback control is continually trying to adjust and correct even under otherwise stable conditions. In this example, this would lead to excess pollution, excess fuel usage and, in the worst case, loss of control of the combustion process with a potentially hazardous outcome.

ii) The installation of the analysers in different locations has increased installation and maintenance costs. These analysers are often in difficult to access locations high up on the stack walls and/or may require special access. Having separate locations will entail extra access time for installation and maintenance. Separate locations will also require extra time and cost for creating the extra access holes and flange attachments.

iii) The analysers may experience different physical ambient conditions such as due to thermal radiation/conduction from the stack wall and exposure to sunlight/shadow/wind, which could lead to significantly different temperature coefficient effects under some circumstances.

iv) The external optical windows of the analysers have to be protected from the aggressive environment of the stack gas. The hazards of this environment include thermal emission from hot stack gas, chemical attack and physical abrasion from particulates. This protection is typically achieved by using a purge gas such as nitrogen, instrument air or other suitable medium, which sweeps past the optical windows and reduces overheating due to heat flow from hot gas stack. The purge gas over external optical windows also helps to keep them clean and unscratched. Having multiple holes in the process wall or stack increases total purge flow consumption and the cost of gas purging.

v) Multiple nozzles in the process wall or pipe and hence multiple windows in contact with the process reduce the robustness of whole measurement system and reduce the safety of the measurements.

An illustration will now be given of the potential increased maintenance costs for an example application. Having two separate locations (entrance and exit holes for the light source and the photodetector) per optical analyser and purge gas supplies for two external optical features increases the cost and complexity of the installation of purge supply. For instance, a typical purge flow rate for protection of a single analyser's optical windows can reach 1000-2000 L/hour per entrance and exit on the heat exchange box of an ethylene cracker furnace. The presence of two or three optical gas analysers with separate entrances and exits leads to a high cost of purge gas supply and complexity of installation of the purge. Thus, in case of installation of three optical analysers with separate entrance and exit holes for each optical analyser, 6000-12000 L/hour supply of nitrogen or instrument air must be arranged. A typical ethylene cracker plant has 12-16 furnaces; therefore installation of three optical analysers on each furnace will lead to very high installation and maintenance costs for only purge gas.

Known systems have typically either provided multiple sources (e.g. diode lasers) and multiple detectors (e.g. photodiodes) within the same housing, or provided an entrance hole and an exit hole for each separate light source. When multiple components are in the same housing, a failure of any one of them is likely to require removal of the complete analyser for repair or replacement, whereas separate entrance holes into the measurement volume for each source and detector has the problems described above. Although optical fibres could be used to direct different laser beams through a single entrance and exit of a measurement volume such as a combustion chamber, there remains a need for careful alignment of the beams.

It is possible with some known systems to achieve synchronised measurement of multiple gases along the same or an equivalent light path, using an analyser that includes multiple components in the same housing. However, these set-ups are inflexible. If a multi-component analyser is installed, it is generally not possible to modify the set-up to detect a different chemical component or set of chemical components that were not in the original specification for the analyser. For example, a prior art multi-component analyser that is installed to measure CO, $H_2O$ and $CH_4$ amount fractions cannot be subsequently modified to additionally measure the amount fraction of NO. To achieve this additional measurement, it would either be necessary to remove the existing multi-component analyser and install a new one capable of making the required measurement set, or install a second independent analyser for measuring NO alongside the existing multi-component analyser. The former option is highly undesirable as it is costly and time consuming to perform the required re-fit, and the latter option suffers from the problems noted earlier in respect of independent analysers.

As mentioned briefly above, one problem with multi-component analysers in a single housing is that failure of one measurement channel in a single multi-component analyser will often require dismounting of the whole analyser for repair and therefore loss of all component information being measured for the duration of the repair. It may be necessary to shut down operations while these repairs are carried out, which is highly undesirable.

SUMMARY OF INVENTION

A first aspect of the present invention provides an attachment and alignment device for mounting a plurality of components of an optical analysis system for optical communication with a measurement volume, to enable performance of multiple optical measurements along aligned optical paths through the measurement volume, wherein the device comprises:

a first attachment point for attaching the device at a position enabling optical communication with a measurement volume;

a mount for mounting an optical alignment device; and a plurality of additional attachment points at distinct angular positions relative to the mount, each of the plurality of additional attachment points enabling attachment of: a light source unit; a light detection unit; or a combination unit comprising at least one light source and at least one detector; to provide a distinct optical path between the mount and each of the additional attachment points; and at least one optical alignment device for mounting on the mount, the optical alignment device being configured to provide optical alignment through the measurement volume of light that passes along said distinct optical paths between the mount and each of the additional attachment points.

A second aspect of the present invention provides an attachment and alignment device for the mounting of a plurality of components of an optical analysis system at one side of a measurement volume, in order to perform multiple optical measurements along a single optical path through the measurement volume. The attachment and alignment device comprises at least the following:

first attachment means to attach the device at one side of a measurement volume for alignment with the optical path;

at least second and third attachment means enabling independent attachment of at least two units which each comprises a light source unit, a light detection unit or a combination unit that comprises at least one light source and at least one detector;

wherein the attachment and alignment device is configured for optical alignment between the optical path and each independently attached light source unit, light detection unit and combination unit.

In an embodiment, the device is configured for optical alignment by a beam splitter held by a beam splitter holder within the device. In some embodiments the beam splitter and beam splitter holder are combined into a single unit. A light source unit may comprise one or more light sources and an attachment means for cooperation with one of the second and third attachment means. A light detection unit may comprise one or more light detectors and an attachment means for cooperation with one of the second and third attachment means, and potentially one or more analysers for processing information from the detector.

As used herein, the term 'light' refers to electromagnetic radiation of any wavelength, and in particular is not restricted to electromagnetic radiation in the visible spectrum.

Embodiments of the invention are advantageous for measurement of the amount fraction of a plurality of different chemical species in a measurement volume, such as absorption spectroscopy measurements using a plurality of different wavelengths of light. Absorption of different wavelengths of light can also be used when measuring a single chemical species, since there are typically a number of different absorption lines than can be detected for a chemical species. The device can also be used for temperature measurement.

Embodiments described herein mitigate the above mentioned problems for simultaneous measurements of multiple species with multiple optical analysers. The following illustrates a number of exemplary embodiments, but it will be appreciated that the invention is not limited to the described embodiments. Instead, a person skilled in the art having the benefit of this disclosure will readily make use of the generic principles illustrated herein to devise other non-illustrated embodiments that are also within the scope of the present invention.

In an embodiment, there is provided a modular optical analysis system comprising the above-described attachment and alignment device and at least two units, each of which comprises a light source unit, a light detection unit or a combined light source and detection unit. The modular system can include a plurality of different light sources and/or a plurality of different light detectors, with independently connectable aligned units enabling different wavelength beams to be transmitted along the same optical path through a measurement volume and enabling different analysis to be performed by an analyser attached to each different detector for the detected light transmitted through the measurement volume.

The modular system provides the flexibility of easily aligned, independently connected and disconnected light source units and light detection units, for greatly improved replacement and repair efficiency. When a decision is made to start measuring an additional or different chemical species, a suitable wavelength light source and detector can be added to the modular system quickly and without having to take the analysis system off-line for a substantial period of time. The same efficiency is provided for replacing a light source with an improved light source, such as when an improved tunable diode laser-becomes available or a higher power of light source is required to cope with high dust load in the process or a larger laser beam divergence is required to cope with high beam deviations due to strong vibration of process walls or high turbulence in the process gas flow. In preferred embodiments, components can be replaced without the need to decouple the attachment and alignment device from the wall of the measurement volume.

The attachment and alignment device includes at least one beam splitter holder. The beam splitter holder may be referred to as a mount. The at least one beam splitter holder may secure in place any combination of the following: at least one beam splitter providing wavelength-dependent transmission and/or reflection of incident light; at least one beam splitter providing wavelength dependent or wavelength independent reflection of incident light; at least one beam splitter providing polarisation-dependent transmission or reflection of incident light; at least one manually adjustable beam splitter providing controlled movement to a defined or optimum position; at least one motorised beam splitter providing controlled or automated movement to a defined or optimum position or oscillation around a defined or optimum position; and/or at least one beam splitter mounted upon a piezo element to oscillate around an average position in order to vary the optical path length thus reducing the effect of optical interference (etalons) in the detected signal.

In an embodiment, the beam splitter holder enables removal and replacement of beam splitters. The beam splitter holder may be slidably arranged within a hollow body of the attachment and alignment device. The beam splitter may be moveable between a plurality of fixed positions and/or its position and orientation may be continuously adjustable.

The measurement of multiple species in a measurement volume such as a process chamber or exhaust duct with optically different wavelength beams being overlapped and being passed along a single optical path or a set of closely aligned optical paths is highly advantageous for reliable, safe, environmentally responsible, and efficient operation. This has particular relevance to hydrocarbon processing furnaces and heaters, but embodiments described herein are not limited to application in these systems. Embodiments may be implemented in any system in which optical spectroscopy is to be performed. In the context of this specification, a first optical path is 'closely aligned' with a second optical path if a light beam aligned along the first optical path will experience a similar or even substantially identical environment as a light beam aligned along the second optical path at any given moment, such that the beam paths are effectively equivalent or interchangeable from a spectroscopic measurement perspective. A spectroscopic measurement conducted along the first optical path at a particular instant would therefore be expected to produce the same or substantially similar result as the same spectroscopic measurement conducted at the same instant along the second, closely aligned optical path. That is, a set of closely aligned optical paths can be treated as a single optical path for the purposes of a spectroscopic measurement. The aforementioned environment may be defined in terms of any combination of the following: physical ambient conditions, thermal properties, average particulate density, elemental composition, gas concentration, gas flow rate and the like. A set of closely aligned optical paths can include two or more optical paths.

The at least one beam splitter is used either to combine at least two separate light beams of different wavelengths together into a single overlapping beam or into a set of closely aligned beams or to separate a combined overlapping beam or a set of closely aligned beams into at least two beams of separate wavelengths. The beam splitter may be a dichroic beam splitter based upon a either an optical flat substrate or a wedged window substrate or upon a prism with reflective coatings or may be a trichroic beam splitter based upon combined dichroic prisms with reflective coatings. In one embodiment a trichroic beam splitter is based upon two combined dichroic beam splitters oriented at a predefined angle. Other suitable beam splitter configurations known to the skilled person may alternatively or additionally be used, such as employing purely reflective surfaces. The beam splitter functions by having wavelength dependent transmission and reflection properties. Such means to separate or combine into overlapping light beams of differing wavelengths are known to those skilled in the art and will not be discussed further here.

The at least one beam splitter is held in place by a beam splitter holder. In some embodiments the holder is an intrinsic part of the body of the device. The holder may be adjustable, in its location (height and horizontal axis rotation) and angle relative to a device axis. This allows the position of the beam splitter to be optimised and then secured in place by suitable means such as a securing screw or screws.

In some embodiments, the beam splitter and/or holder are replaceable components. This allows replacement in the event of damage or if different measurement wavelengths are required. The nominal angle of the beam splitter may be chosen for a specific device configuration. For example, in an application where it is desirable that the device has at least one light transmitter and detector arranged perpendicular to the main body, it is preferable to orient the beam splitter at a nominal angle of 45 degrees relative to the main body axis of the device. Other embodiments may have other preferred nominal angles, for example at the Brewster angle for minimum reflective losses or may be at any other preferred angle to suit the surrounding mechanical arrangement for optical alignment of the beams and the at least one beam splitter.

In some embodiments, two or more beam splitters may be combined within the same assembly to select at least three different optical wavelength measurements. In these embodiments, it is preferred that at least one of the beam splitters should have similar transmission characteristics for at least two of the wavelengths. It will be readily appreciated by one skilled in the art that the same technical effect could also be achieved by combining two or more optical alignment devices together, each containing at least one beam splitter.

In some embodiments, the attachment and alignment device comprises an alignment assembly including a plurality of optical alignment devices. The alignment assembly can include an optical alignment device for each of a plurality of source units or detection units or combination units attached to the additional attachment points. Alternatively, a first source and/or detection unit may have its optical axis aligned with the measurement volume such that it does not require any beam adjustment.

In some embodiments, the attachment means comprise a plurality of welded flanges that are suitable for mechanical attachment (for example for bolting together, or for bolting to a wall or measurement volume). In another embodiment, the attachment and alignment device includes threading for threaded attachment of light source units, detection units, or a transmission unit connected to a wall of a measurement volume. The attachment means may include seals for fluid-tight attachment of the various independently-attachable units. Other embodiments, which use similar or equivalent attachment arrangements known to the skilled person, are also within the scope of this invention. In an embodiment, the attachment means for attaching the device to a wall of the measurement volume is mechanically robust to avoid sagging that can lead to optical mis-alignment, which would result in measurement error. In some embodiments, there is also provided some alignment adjustment means, such as adjustable positional screw mechanisms or similar within the attachment means, to allow a change in angle and/or rotation of the device.

The attachment means for attaching to the wall of the measurement volume includes a seal for ensuring effective sealing of an aperture provided in this wall. This sealing may be achieved by a gasket, adjustable bellows or other suitable method known to the skilled person.

In some embodiments the attachment and alignment device comprises at least one optical component, which may have an anti-reflective coating, and may be one or more of the following: a window and/or optical single or multiple pass band filter and/or lens. Other embodiments may make use of any other suitable optical transmission means which is transparent to the relevant wavelength ranges. The optical component or other light transmission means may be chosen so as to collimate the light output to increase the light intensity at the detector or to diverge the light output to create a larger diffused light cone at the detector for easier optical alignment.

In some embodiments, the device further includes an integrated purge system to maintain the optical component clean and scratch free. The purge may help to manage the surface temperature of the optical component. In some embodiments the purge medium is dry nitrogen or instrument air, but could be any another suitable medium known to the skilled person. Preferably, the purge uses a gas that does not absorb at the required transmitted wavelengths for the measurement. The required purge rate for any individual attachment and alignment device attached to a wall of the measurement volume may be the same regardless of how many light sources or detectors are connected to it, since there is only one device per side opening on the measurement volume. The purge rate can be readily determined according to the specifics of a given setup, using techniques known by the skilled person.

In some embodiments the main body of the device contains at least one beam splitter, which may be contained within a sealed volume. The main body of the device may also be purged with a suitable purge medium and this purge medium may be the same or a different medium as that used for the purge of the optical component. In some embodiments, a single purge input means may be used, which is used to purge both the main body of the device and the optical component.

In some embodiments, additional components including a sealed window or lens transparent to the wavelengths of interest and/or an optical pass band filter and/or an optical diffuser may be provided to make the measurements less subject to optical alignment errors due to, for example, vibrations. The additional components may comprise an adjustable wall mount.

In some embodiments, at least one sealed or purgeable reference cell may be present, which may be fixed in place or movable into the optical path of a light beam using a manual or motorised assembly. Such a sealable reference cell has transmissive surface elements to allow passage of the light beam through the reference cell, or at least one transmissive surface and at least one reflective surface. This reference cell may be used as a "absorption line lock" to fix the light output at a particular wavelength or wavelengths, such as if the reference cell contains at least one measurand or reference medium absorbing within the desired wavelength range. Alternatively, the internally sealed device itself may be continually purged or purged and sealed with the reference medium. Where at least one movable reference cell is used, this may be used as a means of calibration when required and again the reference cell contains at least one measurand and or reference medium absorbing in the desired wavelength range.

In some implementations, at least two attachment and alignment devices are used and sealed together either directly or via at least one intermediate measurement cell and the internal volumes themselves constitute a measurement cell volume for measurand determination. This implementation may include internal reflective surfaces to increase the effective path length via a White cell or Herriott cell or similar arrangement.

BRIEF DESCRIPTION OF THE DRAWINGS

Preferred embodiments of the present invention are described below, by way of example only, with reference to the accompanying drawings in which:

FIG. 3A is a top view cross-section of the device of FIG. 1 illustrating a first set of beam paths;

FIG. 3B is a top view cross-section of the device of FIG. 1 illustrating a second set of beam paths;

FIG. 4A is a schematic view of the device of FIG. 1 as viewed from transmitter TR1 or transmitter TR2 of FIG. 3C;

FIG. 5 is a schematic drawing of a dichroic beam splitter suitable for use with embodiments;

FIG. 13A is a schematic drawing of a triple beam arrangement using reflective and transmissive beam paths.

DETAILED DESCRIPTION OF THE EMBODIMENTS

Figure 1:
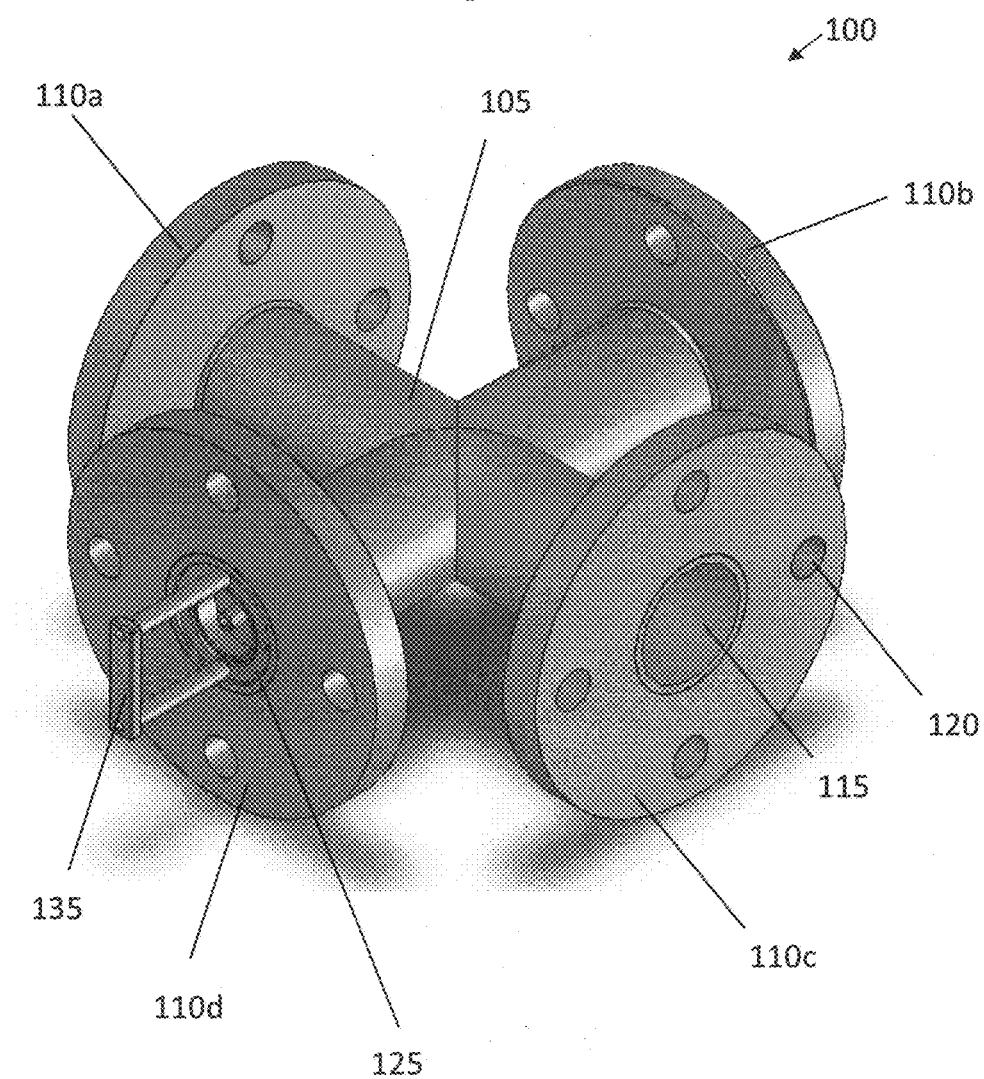
FIG. 1 shows an isometric view of an attachment device according to an embodiment.
Figure 2:
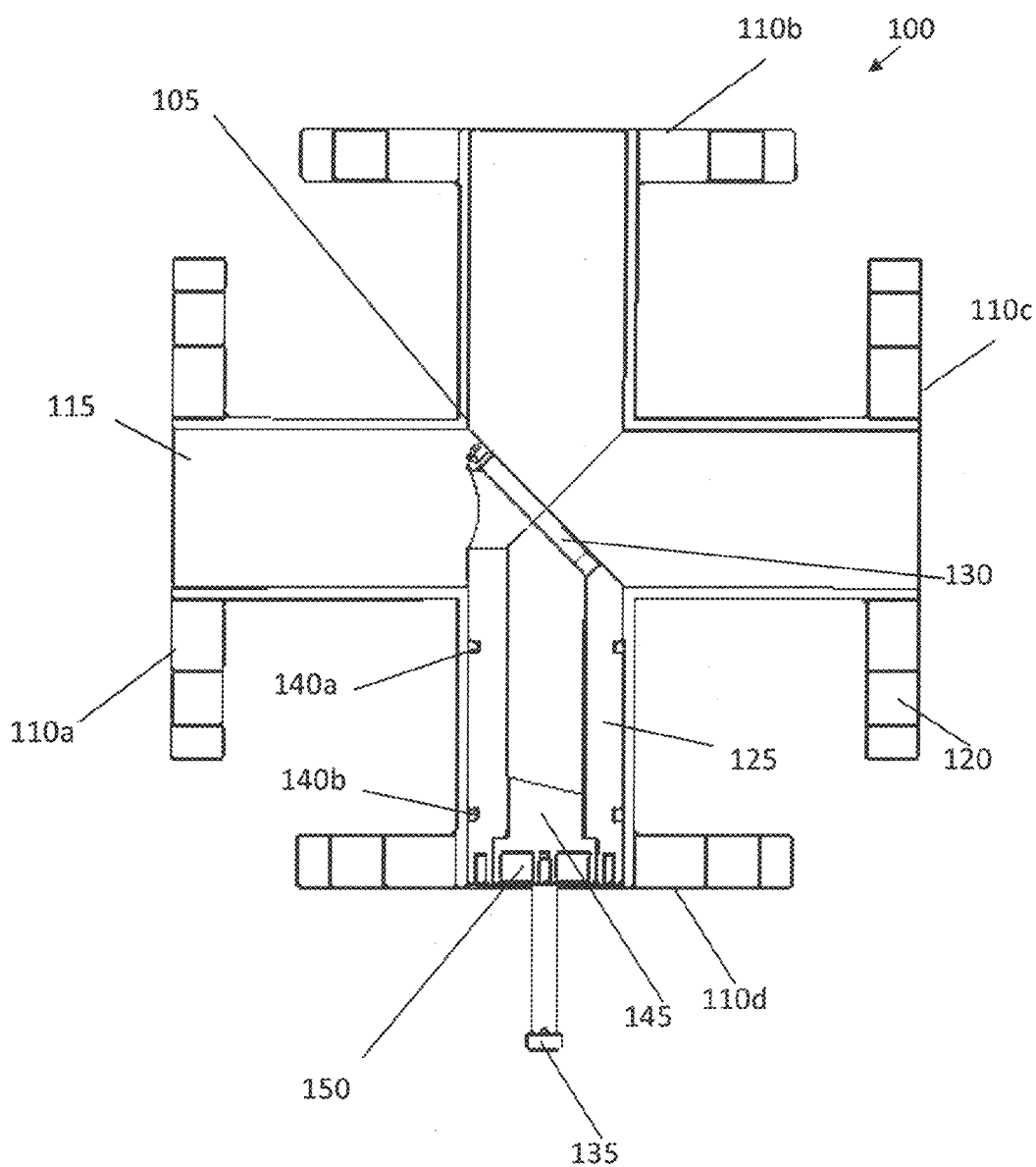
FIG. 2 is a top view cross-section of the device of FIG. 1.

An attachment and alignment device 100 according to an embodiment is shown schematically in FIGS. 1 and 2. Attachment and alignment device 100 comprises a body portion 105 and flanges 110a, 110b, 110c and 110d. In this particular embodiment, body portion 105 is cross-shaped and comprises a pair of hollow cylinders that are arranged at right angles to one another and which intersect at their respective mid-points. It will be appreciated that variations on this arrangement are possible, and other geometries are also within the scope of the invention. Attachment and alignment device 100 may be made of any durable material but is preferably made of metal or metal alloy such as stainless steel.

In this embodiment four flanges 110a, 110b, 110c and 110d are provided, one on the end of each cylinder that forms part of body portion 105. Each flange is circular in this embodiment, but it will be appreciated that the flanges may alternatively have other shapes e.g. square, oval or rectangular. Any number of flanges may alternatively be provided. Flanges 110a, 110b, 110c, 110d can be mounted on a process flange welded either directly onto a wall of the measurement volume (e.g. a process chamber or exhaust duct) or onto a nozzle at an entrance hole in the wall of the measurement volume.

As best shown in FIG. 1, each flange 110a, 110b, 110c, 110d is located at an end of a respective one of the cylinders that make up body portion 105. Each flange includes a through hole 115 that allows the end of a cylinder to extend through the thickness of the respective flange. Preferably the extension is such that the end of the cylinder is flush with the exterior face of the respective end face. In this embodiment, through hole 115 is located approximately at the centre of the relevant flange, but other locations for through holes are also contemplated.

In the embodiment of FIG. 1, the angle between each of the cylinders that make up body portion is 90 degrees. This is not essential to all embodiments, and embodiments having other angles are within the scope of the invention.

Each flange includes attachment through holes 120. These extend through the thickness of each flange and are provided to allow attachment and alignment device 100 to be mounted on an object, e.g. a side wall of a measurement volume. Equally, attachment through holes 120 allow other devices, such as light transmission units, detection units, other identical or similar attachment devices, light source units such as laser light sources, and other such optical components to be mounted to attachment and alignment device 100. In the illustrated embodiment four equally spaced attachment through holes 120 are provided in each flange, but it will be appreciated that any number of attachment through holes 120 can instead be provided. The location of each attachment through hole can also be varied. More specifically, the shape, location, position, number and diameter of each attachment through hole 120 is preferably selected according to both the nature of the attachment means that is to be used to mount attachment and alignment device 100 to various other components and also according to the dimensions, weight etc. of these other components themselves. For example, in one embodiment grub screws are used to secure device 100 to various other components, and the dimensions of through holes 120 are selected so as to match the dimensions of the grub screws.

Attachment and alignment device 100 also includes a carriage 125 that includes a beam splitter 130 (not shown in FIG. 1; see FIG. 2). Carriage 125 also includes a handle 135 that protrudes outwardly from carriage 125 such that it is accessible from the exterior of attachment and alignment device 100. In some embodiments handle 135 is removably attached to carriage 125. Force is applied to handle 135 in the direction away from attachment and alignment device 100 in order to allow carriage 125 to be slidably removed from body portion 105. This allows beam splitter 130 to be accessed for e.g. repair, replacement and cleaning. Grooves 140a, 140b are provided in carriage 125 to allow O-ring seals to be secured around the exterior of carriage 125. Carriage 125 also includes a beam trap 145 to avoid unwanted reflections, and a locking means 150 which in the illustrated embodiment is a grub screw. The beam trap may have any shape or surface coating and such means are known to those skilled in the art. Carriage 125 is discussed in more detail later in connection with FIG. 5. It will be appreciated that more than one carriage 125 can be simultaneously present within attachment and alignment device 100, if desired.

It will be appreciated from FIG. 2 in particular that the hollow nature of body portion 105 allows light such as a laser beam to pass into body portion 105 such that it is incident on beam splitter 130. Light that is incident on beam splitter 130 can then exit attachment and alignment device 100.

Figure 3C:
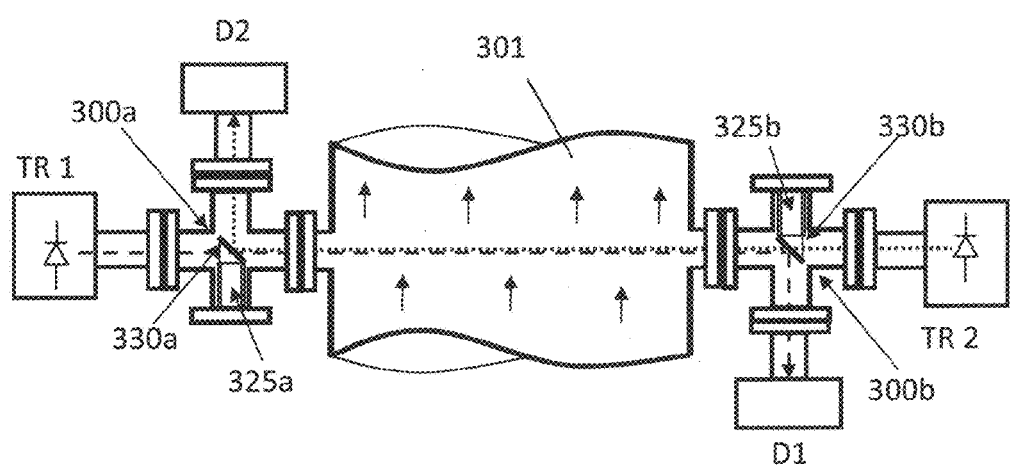
FIG. 3C is a schematic drawing of a dual optical analyser system according to an embodiment.

One exemplary embodiment of a dual optical analyser system is shown in FIGS. 3A, 3B and 3C. The dual optical analyser system comprises a first optical analyser including a transmitter TR1 and a detector D1 and a second optical analyser including a transmitter TR2 and a detector D2. The first optical analyser operates at wavelength λ1 and the second optical analyser operates at wavelength λ2, where λ1≠λ2.

In this particular exemplary embodiment, in the example of FIG. 3A, laser light at wavelength λ1 enters attachment device 300a via flange 310a, is incident upon beam splitter 330a and exits attachment device 300a via flange 310c which could be connected to a transmission unit or directly to a wall of a measurement volume (not shown) so as to pass through the measurement volume. Simultaneously, laser light at wavelength λ2 enters attachment device 300a via flange 310c (from the measurement volume), is incident upon beam splitter 330a and exits attachment device 300a via flange 310b. In this embodiment beam splitter 330a is dichroic, as it allows the laser beam of wavelength λ1 to pass straight through relatively unimpeded but reflects the laser beam of wavelength λ2. Each beam of laser light is produced by a laser (not shown). The dichroic beam splitter may comprise a hard coating deposited on a glass substrate transparent at λ1 and reflective at λ2.

A second attachment device 300b is shown in FIG. 3B and is provided at another point on the process stack. In this particular embodiment, a laser beam of wavelength λ1 enters attachment device 300b via flange 310a (after passing through the measurement volume) and is incident upon beam splitter 330b. Similarly, a laser beam of wavelength λ2 enters attachment device 300b via flange 310c and is incident upon beam splitter 330b. Beam splitter 330b is again dichroic but in this case allows the beam component of wavelength λ2 to pass straight through relatively unimpeded but reflects the beam component of wavelength λ1. The result is that a beam of wavelength λ1 exits attachment device 300b via flange 310b (where it can be detected by an attached detection unit (not shown) and a beam of wavelength λ2 exits attachment device 300b via flange 310a to pass through the measurement volume. The dichroic beam splitter may comprise a hard coating deposited on a glass substrate transparent at λ2 and reflective at λ1.

Dual optical analyser systems have application in many areas. One such area is continuous measurement of gas species in combustion systems, where it can be vital for safe and efficient operation in combustion systems to know the constituents of a combustion gas. While not limited thereto, the instant invention can be important in hydrocarbon processing furnaces and heaters, power stations and other combustion based processes.

For measurements of oxygen ($O_2$), carbon monoxide (CO) and/or water ($H_2O$) and/or hydrocarbons such as methane ($CH_4$) or ethylene ($C_2H_4$) including gas temperature along a single optical path, a dual optical analyser arrangement including two optical analysers and two attachment devices 330a, 330b such as shown in FIG. 3C can be used. Such multiple measurements based upon two optical analysers are in particular interest for in-situ measurements in hydrocarbon processing heater or furnace such as in an ethylene cracker furnace, a petroleum refinery heater, a petroleum refinery hydrocracker, a petroleum refinery fluidised catalytic cracker and an electrical power generation steam boiler. For efficiency of combustion process monitoring of $O_2$, CO concentration and gas temperature are most important. An optical analyser based upon tuneable diode laser absorption spectroscopy and diode laser emitting at approximately 760 nm and scanning over few $O_2$ absorption lines can be used for $O_2$ concentration measurements and for extraction of spectral gas temperature averaged over optical path length through the process gas.

CO and/or $H_2O$ and/or $C_2H_4$ can be measured by an optical analyser based upon tuneable diode laser wavelength modulation spectroscopy having a diode laser at 2.3 μm scanning over CO, $H_2O$ and $C_2H_4$ absorption lines within a single wavelength scan. Thus, an optical analyser formed by a transmitter TR1 and a detector D1 and based upon diode laser emitting light at wavelength of 760 nm can be used for measurements of $O_2$ and spectral temperature, and an optical analyser formed by transmitter TR2 and detector D2 based upon a diode laser emitting at a wavelength of approximately 2.3 μm can be used for measurements of CO, $H_2O$ and hydrocarbons.

FIG. 3C shows attachment device 300a and 300b mounted in a dual analyser system. Two light sources TR1, TR2 of different wavelengths are attached to a respective one of attachment device 300a, 300b. In some embodiments TR1 and TR2 are laser light sources such as tunable diode lasers. Other light sources known to the skilled person can alternatively be used instead.

Attachment devices 300a, 300b are both substantially identical to attachment and alignment device 100. The light beams emitted by TR1, TR2 are combined by a beam splitter 330a comprising a first dichroic beam splitter (described later in connection with FIG. 8A) into a combined overlapping light beam. This light beam is aligned by design or through adjustment with the pair of attachment devices 300a, 300b across the measurement volume 301. Measurement volume 301 includes a pair of process flanges or nozzles (not shown) that are each placed around a hole in measurement volume. The pair of holes in measurement volume provide an entrance and exit to the interior of measurement volume 301. Attachment devices 300a, 300b are each connected to measurement volume 301 by a process flange. Absorption by any measurands present may occur as this combined light beam crosses from the first attachment device 300a to the second attachment device 300b across the measurement volume 301.

This combined beam is then split into two separate light beams of the two respective wavelengths by a beam splitter 330b comprising a second dichroic beam splitter (described later in connection with FIG. 8A) that is located in second attachment device 300b. These separate beams are then directed to two respective detectors D1, D2 for the two different wavelengths and the respective absorptions measured. From these measurements, parameters relating to the measurands such as amount fraction may be determined.

The overall operation of the dual analyser system is as follows. The optical beam with wavelength λ1 is emitted by transmitter TR1 and passes through beam splitter 330a to enter the measurement volume 301 via a process hole or nozzle. The beam with wavelength of λ1 then passes through the measurement volume 301, which in some embodiments is a combustion chamber, and then exits through another process hole or nozzle into attachment device 330b. The optical beam with wavelength λ1 is then reflected by beam splitter 330b towards detector D1. Simultaneously, the optical beam with wavelength λ2, which is emitted by transmitter TR2, passes through beam splitter 330b and enters the measurement volume 301 via a process hole or nozzle. The beam with wavelength of λ2 then passes through the measurement volume 301 and then exits through another process hole or nozzle into attachment device 300a. The optical beam with wavelength λ2 is then reflected by beam splitter 330a towards detector D2.

In some embodiments, the light beams may be optimally aligned by adjustment of the position and orientation of the at least one of the dichroic beam splitters 330a, 330b and/or the alignment and orientation of at least one of the attachment devices 300a, 300b may be adjustable at the point at which the relevant attachment device is mounted to the side of the measurement volume 301.

In order to maximise light intensity passed through the probed medium, positions of the dichroic beam splitters 330a, 330b are preferably optimised relative to the optical beam axes by translating the beam splitter holders towards the detectors D1, D2 and across the optical beams of the TR1 and TR2 or by twisting the beam splitter holders in the pipe-cross arm opposite to the detector D1 and to the detector D2 using a handle which can be mounted on a base of each beam splitter holder.

In some embodiments an automated beam splitter adjustment procedure is employed. This makes use of a motor that is arranged such that it is able to adjust the position of the beam splitter holder relative to an optical beam axis. The motor is controlled by a control unit, which is also connected to an output of a detector or detectors. The detector may be the abovementioned detector D1 or detector D2 or a separate detector unit, or a combination of output signals may be employed. The detector is configured to measure incident light intensity or intensities as a function of the position of the beam splitter, such that a feedback loop can be employed to determine the optimal position of the beam splitter. Specifically, the motor may adjust the position of the beam splitter until maximal signal intensity is detected by the selected detector or a maximal average signal intensity is detected by the selected detectors.

Figure 4B:
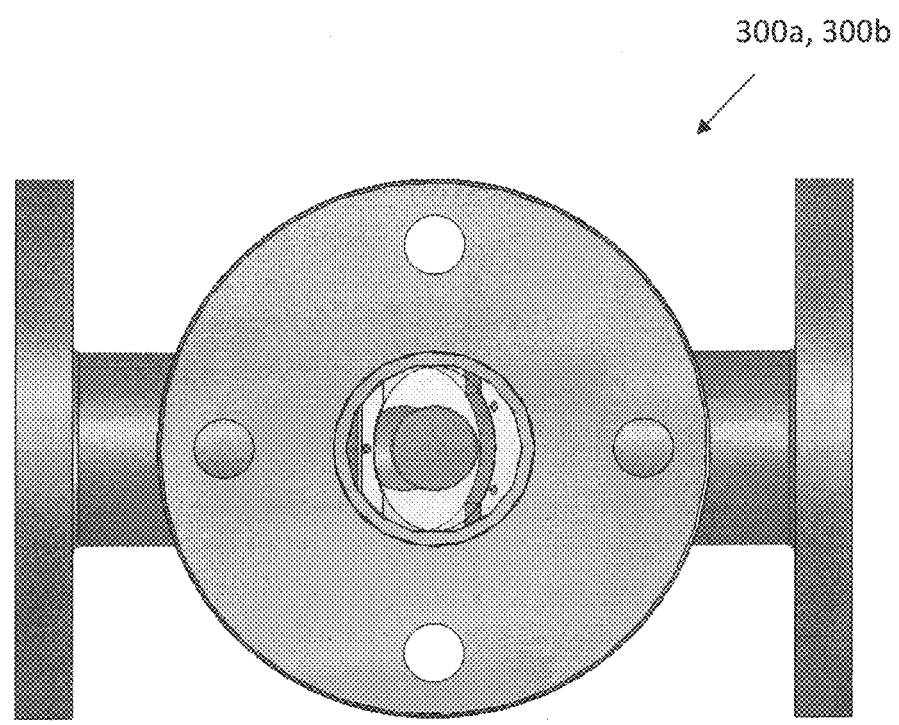
FIG. 4B is a schematic view of the device of FIG. 1 as viewed from detector D1 or detector D2 of FIG. 3C.

Typical views of attachment devices 300a, 300b from the transmitters TR1, TR2 and the detectors D1, D2 are shown in FIGS. 4A and 4B, respectively.

In one particular embodiment, suitable for measurements of oxygen ($O_2$), carbon monoxide (CO), water ($H_2O$) and hydrocarbons such as methane ($CH_4$) or ethylene ($C_2H_4$) including gas temperature along single optical path, transmitter TR1 emits laser light at 760 nm and transmitter TR2 emits laser light at 2.3 µm. Detector D1 is tuned to detect light at 760 nm, and detector D2 is tuned to detect light at 2.3 µm. In this embodiment, beam splitter 330a has maximum transmission at 760 nm and maximum reflection at 2.3 µm and beam splitter 330b has maximum transmission at wavelength of 2.3 µm and maximum reflection at wavelength of 760 nm.

In a variant of this embodiment, two identical beam splitters that both have maximum transmission at 760 nm and maximum reflection at 2.3 µm are used in place of beam splitters 330a, 330b. In this variant embodiment, the position of transmitter TR2 and detector D1 on attachment device 300b are interchanged with respect to that shown in FIG. 3C.

In a further variant, two identical beam splitters with maximum transmission at 2.3 µm and maximum reflection at 760 nm are used. In this further variant, the position of transmitter TR1 and detector D2 are interchanged with respect to that shown in FIG. 3C. Such interchangeability of the beam splitters 300a, 300b provides flexibility in service of the attachment and alignment devices of dual optical analyser arrangement for measurements at wavelengths of 760 nm ($O_2$ plus spectral temperature) and 2.3 µm (CO, $H_2O$ and hydrocarbons such as $CH_4$ and $C_2H_4$).

In order to prevent contamination of the beam splitters and the output optical windows of the analysers, purge flow of the attachment devices 300a, 300b is preferably arranged from both sides of the measurement volume 301. This can be done by insertion of two additional purge flanges (not shown) between each of the process flanges (not shown) on measurement volume 301 and the flange of attachment devices 300a, 300b, respectively, that is connected to one of the process flanges. The purge flanges can have one or more channels, which may be arranged from an outer surface to the flange bore, for purge gas flowing to a nozzle and then to a combustion chamber. In other cases, purge flow arrangements, used for protection of the transmitter and the receiver optical windows and mounted on the transmitter and the receiver for each analyser, can be used as supplied as purge gas flow can freely flow over and around the beam splitter mounted in the attachment and alignment device.

In case of offset of the entrance hole/nozzle relative to the exit hole or nozzle on the measurement volume 301, or in case of poorly co-aligned nozzles on the measurement volume 301, alignment means based upon relative displacement of the analyser flange and the process mounting flange can be used with an optical analyser for correction of such offsets and misalignments.

Optical beams can sometimes deviate/or steer when propagating through a hot and turbulent gaseous medium such as is found in a combustion chamber. Such deviations can result in loss of light intensity incident on the detectors and hence lead to loss of measurements. Also, creeping and vibrations of the furnace walls may lead to drift and jitter of optical beam alignment of the optical analysers and hence lead to loss of measurements. In order to avoid loss of measurements due to optical misalignment induced by mechanical movements of chamber walls and the process nozzles, optical beams of both optical analysers can be deliberately diverged to have a laser beam diameter at the detector side that is a few times larger than the detector optics aperture. This keeps the optical beam light intensity incident over the detector's apertures at high levels despite optical beam deviation or steering. In one particular embodiment, the divergence is in the range of 20 mm to 40 mm over four meters. This not only maintains a degree of alignment to avoid loss of measurements, the divergent beams may also be useful during initial set-up and to detect deviations as they start to occur, avoiding a sudden loss of measurements.

The dual optical analyser of FIG. 3C is also suitable for the simultaneous measurements of ammonia ($NH_3$) and nitric oxide (NO). This is of great interest for optimising nitrogen oxide ($NO_x$) abatement in combustion based processes. Often these combustors use selective non-catalytic reduction or selective catalytic reduction for converting $NO_x$ into diatomic nitrogen ($N_2$) and water. These $NH_3$ and NO measurements can be performed along a single optical path through a measurement volume such as an exhaust duct by mounting two independent optical analysers and two attachment devices in accordance with the schematic shown in FIG. 3C.

In this particular embodiment, the first optical analyser that includes TR1 and D1 performs wavelength modulation absorption spectroscopy as transmitter TR1 is a diode laser emitting at wavelength of 2.25 μm. This is suitable for $NH_3$ measurements. The second optical analyser that includes TR2 and D2 performs tuneable laser absorption spectroscopy as TR2 is a quantum cascade laser emitting at wavelength 5.2 μm, which is suitable for making NO measurements.

In this particular embodiment, beam splitter 330a has a maximum transmission at approximately 2.25 μm and a maximum reflection at approximately 5.2 μm, whilst beam splitter 330b has maximum transmission at wavelength of approximately 5.2 μm and maximum reflection at wavelength of approximately 2.25 μm. In this specific embodiment detector D1 is a InGaAs photodetector that is suitable for detection of a laser beam at approximately 2.25 μm, and detector D2 is a thermoelectrically cooled HgCdZnTe photovoltaic detector that can be used for detection of a laser beam at approximately 5.2 μm.

Dual optical analyser systems that include two attachment devices (see FIGS. 3C, 7 and 9) and have beam splitters based upon a glass substrate or a reflective prism are not limited to use in only the examples described above. These dual optical analyser systems are also suited for measuring 1) $O_2$ plus spectral temperature at 760 nm and either-CO and $C_2H_4$ and $H_2O$ or CO and $CH_4$ and $H_2O$ at 2.3 μm; 2) $NH_3$ measurement at 2.25 μm and NO detection at 5.2 μm; 3) $H_2O$ detection at 1.3 μm and $NH_3$ monitoring at 2.25 μm, 4) $H_2O$ detection at 1.87 μm and $CH_4$ detection at 1.65 μm, 5) CO detection at 2.3 μm and $CH_4$ monitoring at 1.65 μm, 6) $H_2O$ detection at 1.3 μm and NH, monitoring at 10.3 μm. Other uses for the dual optical analyser systems according to embodiments will be apparent to the skilled person having the benefit of the present specification.

An equivalent arrangement to the embodiment of FIG. 3C includes one light source at a first wavelength and one detector at a second wavelength attached to a first attachment device and one detector for the first wavelength and one source for the second wavelength attached to the second attachment device.

Further modifications to this embodiment include replacing at least one light source or at least one detector by a single housing containing multiple sources and/or multiple detectors. In this instance, it is preferable that the beam splitters used have similar transmission and reflective properties for the two or more wavelengths used by the single housing.

It will be readily apparent to someone skilled in the art having the benefit of the present disclosure that several similar arrangements may be made using more than one attachment device like attachment device 100 in series and/or in parallel or using attachment devices like attachment device 100 that include multiple beam splitters which will enable the measurement of more than two measurands simultaneously with an identical optical pathway through a measurement volume. Some embodiments may have the means to blank off at least one attachment position in an attachment device in order to avoid the impact of stray light and/or contamination on the other measurements. In some embodiments, the blanking means may be sealed. In one embodiment an attachment position is provided with a blanking and sealing attachment for sealing with at least one optical component, which may have an anti-reflective coating, and may be one or more of the following: a window and/or a single or multiple pass band filter and/or a lens transparent to the wavelengths of interest. In another embodiment an attachment position is provided with a blanking and sealing attachment for sealing with a diffuser transparent to the wavelengths of interest.

It is also possible to use alternative geometries to mount the two devices, whereby they are not directly optically aligned across a measurement volume, but optically aligned via a reflective means, such as a plain or shaped mirror or combination of mirrors. This reflective alignment means may also be adjustable. This may be required due to spatial constraints of the surroundings of the measurement volume or to obtain increased pathlength and hence increased sensitivity of the measurement. For example, the two devices could be situated on the same circumference of a circular cross section measurement volume and have their main device optical axes aligned at equal angles and opposite sides relative to the normal of a flat mirror allowing optical alignment between the two devices.

It will be appreciated that the embodiment of FIGS. 3A to 3C illustrates only one of a great number of possible different beam configurations achievable by the present invention. As a result, numerous modifications will be readily apparent to the skilled person having the benefit of the present disclosure. Moreover, it will also be appreciated that any number of attachment devices identical or similar to attachment device 100 can be provided in a single system in order to provide any desired arrangement of beams, further increasing the number of possible alternative configurations. Some further exemplary configurations are discussed later in this specification with reference to FIGS. 6, 7 and 9-12.

FIG. 5 is a schematic view of a beam splitter element 550 suitable for use with embodiments described herein. Beam splitter 550 includes a cylindrical carriage 555 that has a handle 560 attached to one end of carriage 555. Handle 560 is preferably removably attached to carriage 555. The outer surface of carriage 555 includes two grooves 565a, 565b for accepting O-ring seals (not shown). It will be appreciated that any number of grooves, including zero, may instead be present. When present, the O-rings placed in grooves 565a, 565b on the body of carriage 555 assist in enabling smooth movement and consistent, stable positioning of beam splitter 550 within an attachment device like attachment device 100.

Beam splitter 550 also includes a reflective optical element 570 that serves to split out at least one wavelength component of a polychromatic incoming beam. In some embodiments reflective optical element 570 is polychroic glass and a silica substrate or calcium fluoride or other optical materials could be used. In one particular embodiment reflective optical element 570 is dichroic glass, and in another particular embodiment reflective optical element 570 is trichroic glass. The glass itself is chosen according to the wavelengths of light that beam splitter 550 is expected to encounter when in use, as would be readily understood by a skilled person having the benefit of the present disclosure. The glass splits a beam by transmitting one more wavelength components of the beam and reflecting one or more different wavelengths components of the beam.

As shown in FIG. 5, optical element 570 is arranged at a non-zero angle with respect to the longitudinal axis of carriage 555. In some embodiments the angle between the longitudinal axis of carriage 555 and the plane of optical element 570 is 45 degrees. This is however not critical, and embodiments having other angles are also contemplated. Preferably the angle between the longitudinal axis of carriage 555 and the plane of optical element 570 is chosen based on the orientation of incoming and outgoing beams.

Carriage 555 preferably includes a locking mechanism to ensure that beam splitter 550 is held securely in place when inserted in an attachment device such as attachment device 100. In the illustrated embodiment the locking mechanism comprises at least one hole 575 in an outer surface thereof, preferably near the end of the carriage 555 that is distal from optical element 570. The at least one hole 575 is dimensioned and located such that it can accept a grub screw (not shown) in order to lock carriage 555 in place in an attachment device like attachment device 100. In some embodiments four holes are arranged around the perimeter of carriage 555. Adjustment of the grub screws allows beam splitter 550 to be fixed in position after all components of the optical analyser system have been correctly aligned.

In order to minimise effects of background light that might otherwise pass between the exterior surface of the beam splitter 550 and the internal surface of the attachment and alignment device 100, in some embodiments handle 560 can be removed once beam splitter 550 is secured in place in an attachment device such as attachment device 100. The face of beam splitter 550 that is exposed when handle 560 is removed is then preferably covered by a blank flange (not shown) that is inserted in carriage 555 proximate the exposed end of beam splitter 550. The blank flange preferably has a rough surface cut at a specific angle with respect to the longitudinal axis of carriage 555. The surface preferably strongly absorbs at least light at and near to the wavelengths of the beam that is expected to be encountered by beam splitter 550. Such a blank flange substantially reduces the chance of light from the beam being reflected or scattered back to a transmitter or detector. This is desirable as such scattered or reflected light can increase measurement noise due to potential optical feedback.

In some embodiments a blank flange is additionally or alternatively placed over the flange of attachment device 100 that is proximate the exposed end of beam splitter 550 once handle 560 has been removed. This blank flange serves to seal the attachment device 100 and as such can have any surface finish and be formed of any suitable material.

Figure 6:
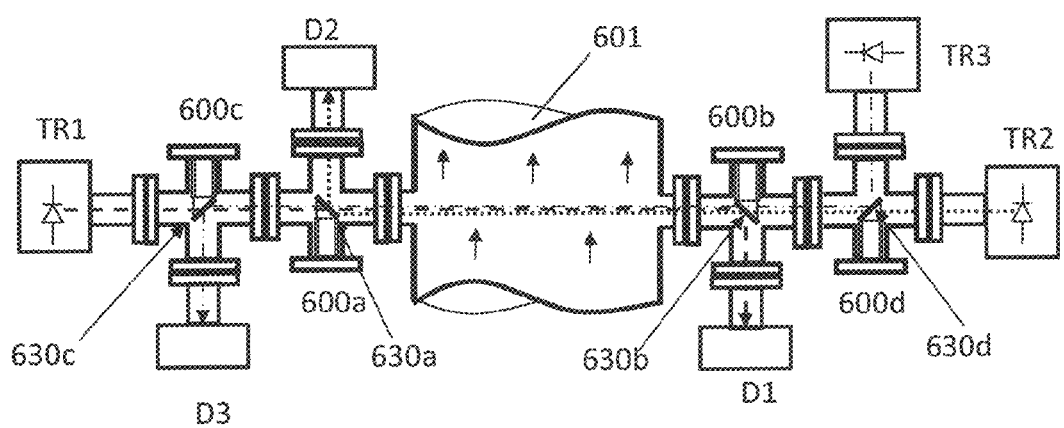
FIG. 6 is a schematic drawing of a triple optical analyser system according to an embodiment.

FIG. 6 shows an arrangement for making triple optical analyser measurements by means of three optical analysers at wavelengths of $\lambda 1$, $\lambda 2$ and $\lambda 3$ according to an embodiment. In this embodiment, four attachment devices 600a, 600b, 600c and 600d are provided, each including a specific dichroic beam splitter 630a, 630b, 630c, 630d. Three transmitters TR1, TR2, TR3 and three detectors D1, D2, D3 are present.

It will be appreciated that the arrangement of FIG. 6 is a modification of the dual optical analyser arrangement shown in FIG. 3C. The additional transmitters and detectors can be readily added to the dual optical analyser arrangement shown in FIG. 3C without any modification of the entrance and exit holes or nozzles on the process. Thus, embodiments described herein allow a dual optical analyser system such as shown in FIG. 3C to be readily modified to a triple optical analyser system without needing to perform a full re-fit. Moreover, a common optical path is used for all beams, avoiding the abovementioned problems associated with independent analysers.

Specifically, to adapt the arrangement of FIG. 3C such that it becomes the arrangement of FIG. 6, firstly transmitters TR1 and TR2 are dismounted. Secondly, attachment devices 600c, 600d are inserted and mounted onto the flanges of the attachment devices 600a, 600b, respectively.

It will be appreciated by the skilled reader that beam splitters 630a-630d should be chosen in order to ensure that the correct components of the composite beam are incident on the appropriate detectors. In the illustrated embodiment, TR1 and D1 form a first optical analyser system, TR2 and D2 form a second optical analyser system and TR3 and D3 form a third optical analyser system. TR1 emits laser light of wavelength $\lambda 1$, TR2 emits laser light of wavelength $\lambda 2$ and TR3 emits laser light of wavelength $\lambda 3$. Each optical analyser system is tuned to an absorption line of a particular chemical species, allowing simultaneous detection and characterisation of multiple chemical species.

Beam splitter 630a mounted in attachment device 600a has maximum transmission at wavelengths $\lambda 1$ and $\lambda 3$ used for measurements by means of the first and third optical analyser systems and maximum reflection at wavelength $\lambda 2$ used for measurements by means of the second optical analyser system. Beam splitter 630b mounted in attachment device 600b has maximum transmission at wavelengths $\lambda 2$ and $\lambda 3$ used for measurements by means of the second and third optical analyser systems and maximum reflection at wavelength of $\lambda 1$ used for measurements by means of the first optical analyser system. Beam splitter 630c mounted in attachment device 600c has maximum transmission at wavelength $\lambda 1$ used for measurements by the first optical analyser system and maximum reflection at wavelength of $\lambda 3$ used for measurements by the third optical analyser system Beam splitter 630d mounted in attachment device 600d has maximum transmission at wavelength $\lambda 2$ used in optical measurements by the second optical analyser system and maximum reflection at wavelength $\lambda 3$ used for measurements by the third optical analyser system.

It will be apparent that the embodiment of FIG. 6 is only one of a great number of possible configurations according to the present invention. Different variation of the beam splitters 630a, 630b, 630c, 630d and arrangements of the detectors D1, D2, D3 and transmitters TR1, TR2, TR3 can be selected to provide other, non-illustrated embodiments. Such additional embodiments are selected according to the specific requirements of a given analyser system and will be apparent to a skilled person upon reading the present specification. Advantageously, the removable nature of carriage 125 means that it is quick and easy to swap out one particular beam splitter for another, meaning that adaptation of an optical analyser system according to the present invention is readily carried out in-situ with minimal downtime.

Figure 7:
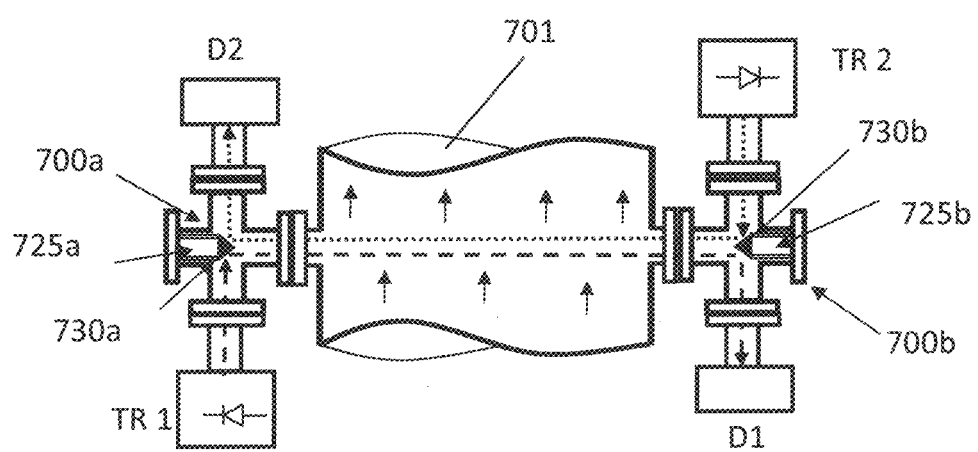
FIG. 7 is a schematic drawing of another dual optical analyser system according to an embodiment.

An alternative dual optical analyser arrangement according to an embodiment is shown in FIG. 7. This dual optical analyser arranging includes a first optical analyser system comprising TR1 and D1 scanning at wavelength $\lambda 1$ and a second optical analyser system comprising TR2 and D2 scanning at wavelength $\lambda 2$. Two attachments devices 700a, 700b are included in the embodiment of FIG. 7, each having a respective carriage 725a, 725b including a respective beam splitter 730a, 730b. In this embodiment, the beam splitters 730a, 730b are both right angled prisms of the type shown in FIG. 8A.

In one specific dual optical analyser embodiment the arrangement of FIG. 7 is used for simultaneous dual measurements of $O_2$ at 760 nm and CO, $H_2O$, and $CH_4$ or $C_2H_4$ at 2.3 µm. In another specific dual optical analyser embodiment the arrangement of FIG. 7 is used for simultaneous dual measurements of $NH_3$ at approximately 2.25 µm and NO at approximately 5.2 µm. In these embodiments beam splitters 730a, 730b may each be right angle prisms with sides coated by either silver or gold. In order to increase robustness of the measurements to mechanical drifts and vibrations laser beams can be diverged as described earlier in this specification.

In some cases, the use of a beam splitter based upon a glass substrate like that shown in FIG. 5 may not be feasible because of, for example, difficulties to manufacture optimal reflection/transmission coating, or a specific beam splitter may be not commercially available. In such cases, a right angle prism like that shown in FIG. 8A can be used in place of the beam splitter of FIG. 5.

Figure 8A:
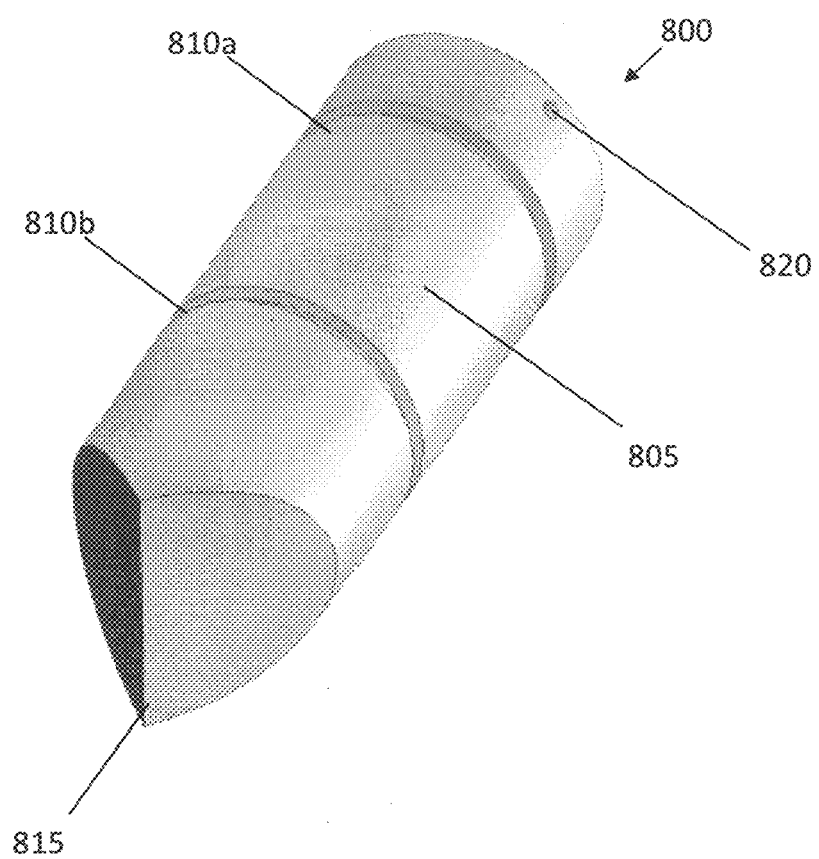
FIG. 8A is a schematic drawing of a right angled prism beam splitter suitable for use with embodiments.

FIG. 8A shows a right angled prism beam splitter 800 comprising a carriage 805. Carriage 805 is cylindrical and includes a pair of circumferential grooves 810a, 810b that each accept an O-ring seal (not shown). One end of carriage 805 tapers inwardly to a common edge to form a right angled prism 815 having two faces. Each face reflects a specific wavelength of light. The wavelength reflected by one face is different to that of the other.

Each face is coated with a high reflective coating. Reflective coating on the prism sides can have either maximum reflection at specific wavelength of each optical analyser (e.g. $\lambda 1$, $\lambda 2$, etc.) or maximum reflection for both wavelengths of both optical analysers.

Carriage 805 preferably includes a locking mechanism to ensure that beam splitter 800 is held securely in place when inserted in an attachment device like attachment device 100. In the illustrated embodiment the locking mechanism comprises at least one hole 820 in an outer surface thereof, preferably near the end of the carriage 805 that is distal from right angled prism 815. The at least one hole 820 is dimensioned and located such that it can accept a grub screw (not shown) in order to lock carriage 805 in place in an attachment device like attachment device 100.

Carriage 805 includes a removable handle (not shown) that is removably attached to the end of carriage 805 that is distal from the end of carriage 805 that includes right angled prism 815. The handle is attached when carriage 805 is slidably inserted into and removed from an attachment device like attachment device 100, and is then removed when carriage 805 is secured correctly in place.

It is not essential that a right angled prism be used in beam splitter 800. Embodiments having prisms with angles other than 90 degrees are also contemplated. Preferably these beam splitters are used in embodiments that make use of attachment devices like attachment device 100 of FIG. 1, but where the cylinders of body portion 105 are not arranged at 90 degrees with respect to one another.

Beam splitters based upon a right angle prism with reflective coatings on the sides of each prism can be inserted into an attachment device like attachment device 100, positioned accordingly, twisted and finally aligned and locked to keep optimal alignment between transmitters and detectors arranged according to any of the embodiments of the present invention.

Figure 8B:
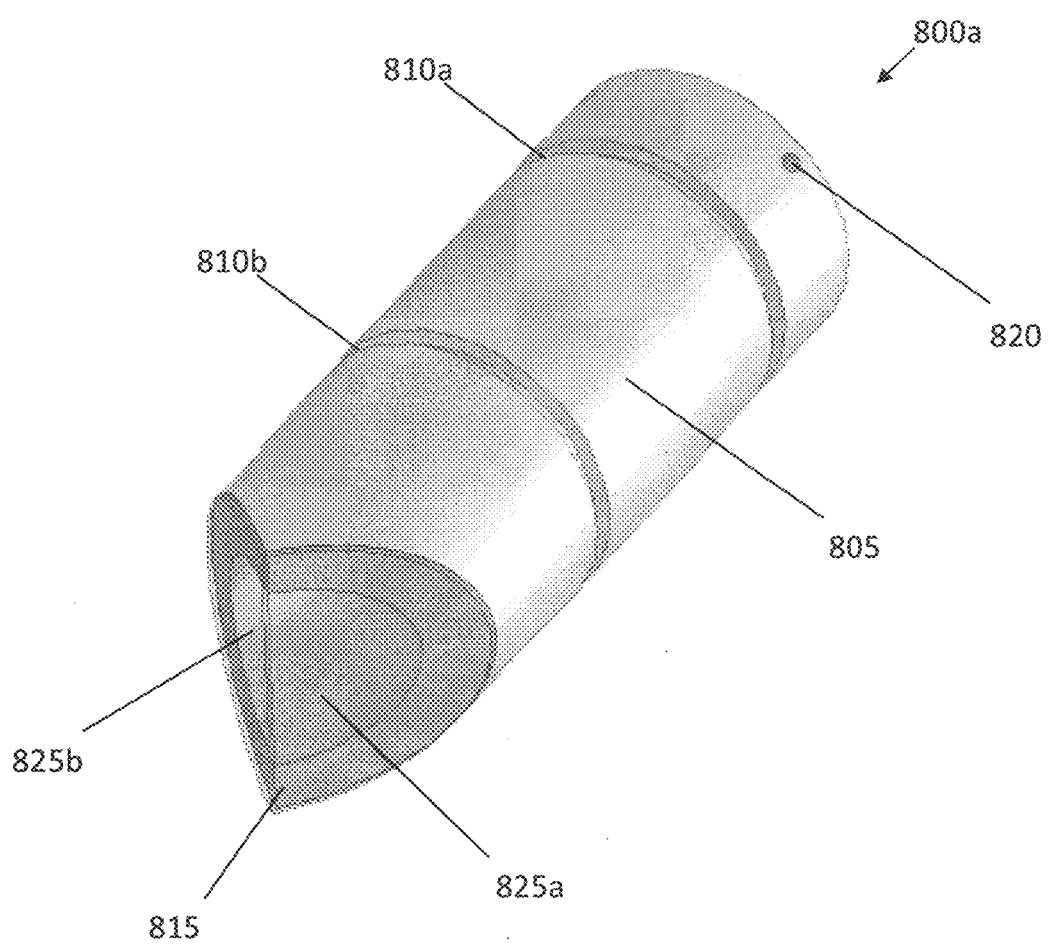
FIG. 8B is a schematic drawing of another beam splitter suitable for use with embodiments.

The dual optical analyser arrangement shown in FIG. 7 can be readily upgraded into a new arrangement with three optical analysers (see FIG. 9) by replacing the right angled prism beam splitters 730a, 730b with a modified beam splitter 900 as shown in FIG. 8B. The modified beam splitter 800a is similar to right angled prism beam splitter 800, but includes a pair of dichroic windows 825a, 825b that are embedded in prism 815. Dichroic windows 825a, 825b can be mounted or glued at 90° on the prism-shaped end of carriage 805. Dichroic window 820a has maximum reflectivity at a wavelength $\lambda 1$ and dichroic window 820b has maximum reflectivity at a different wavelength $\lambda 2$, where $\lambda 1 \neq \lambda 2$. Both dichroic windows 820a, 820b have maximum transmission at another wavelength $\lambda 3$, where $\lambda 3$ is different from both $\lambda 1$ and $\lambda 2$.

Figure 9:
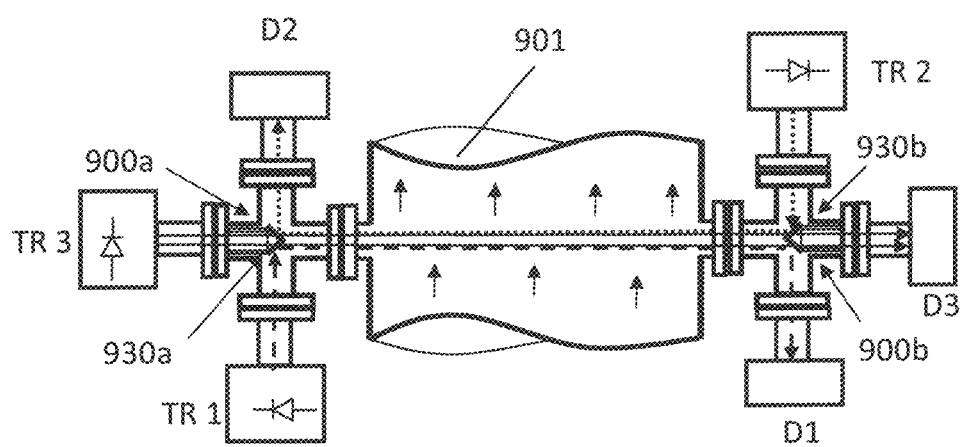
FIG. 9 is a schematic drawing of another triple optical analyser system according to an embodiment.

FIG. 9 shows another three optical analyser embodiment that is an upgraded version of the dual optical analyser embodiment of FIG. 7. A first optical analyser system comprises transmitter TR1 and detector D1, a second optical analyser system comprises transmitter TR2 and detector D2 and a third optical analyser system comprises transmitter TR3 and detector D3. The first, second and third optical analyser systems are tuned to wavelengths $\lambda 1$, $\lambda 2$ and $\lambda 3$, respectively, $\lambda 1 \neq \lambda 2 \neq \lambda 3$. The embodiment of FIG. 9 includes two attachment devices 900a, 900b that each include a beam splitter 930a, 930b of the type shown in FIG. 8B.

The dual optical analyser system of FIG. 7 can be upgraded into the triple optical analyser system of FIG. 9 as described in the following. After alignment of the first and second optical analyser systems by translating and twisting the carriages of beam splitters 930a, 930b, the carriages are locked in place. Locking can be achieved using locking mechanism 820. The handle (not shown in FIG. 9) on each beam splitter 930a, 930b is then removed to allow transmitter TR3 and detector D3 to be mounted to a respective one of attachment device 900a, 900b. TR3 and D3 are then co-aligned on the flanges of the respective attachment devices 900a, 900b to produce the arrangement shown in FIG. 9. The net result is that three simultaneous optical measurements by three optical analysers can be performed by means of three independent optical analysers aligned along a common optical path. The modification work is quick and easy to perform and does not require a complete re-fit of the existing dual optical analyser system. Moreover, if it subsequently becomes desirable to replace e.g. the first optical analyser system comprising TR1 and D1 with a different optical analyser system comprising transmitter TR4 and detector D4, operating at a wavelength $\lambda 4$, this is also possible without a complete re-fit of the triple optical analyser system.

Figure 10:
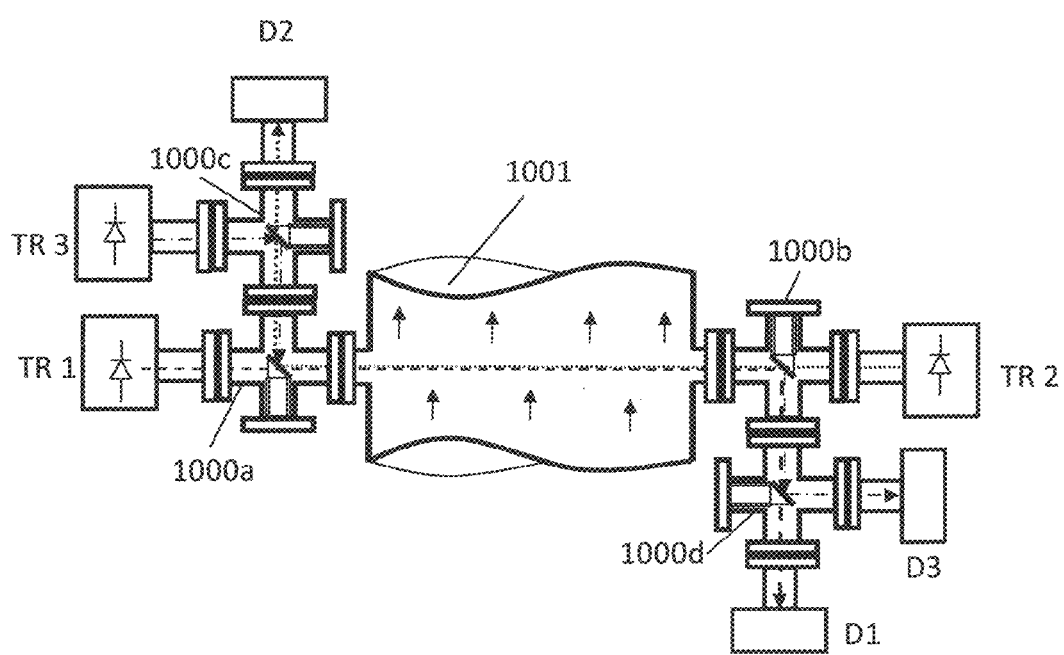
FIG. 10 is a schematic drawing of yet another triple optical analyser system according to an embodiment.

In some cases space restrictions mean that it is not possible to mount three optical analysers in an arrangement like that shown in FIG. 6. In such cases an arrangement like that shown in FIG. 10 can instead be used. As shown in FIG. 10, transmitters TR1 and TR3 are located on one side of the measurement volume 1001 and transmitter TR2 and detector D3 are located on the opposite second side of the measurement volume 1001. TR1 and TR2 are located at the same distance from the wall of measurement volume 1001, and transmitter TR 3 and detector D3 are located at the same distance from the wall of measurement volume 1001. Detector D1 and Detector D2 are mounted closer to the wall of the measurement volume 1001 than any of TR1, TR2, TR3 or D3. Thus, the modular nature of the present invention advantageously introduces a flexibility that allows an existing system to be upgraded regardless of space constraints. This advantageously means that it is not necessary to completely re-fit an existing system when performing upgrade work.

Use of a third optical analyser can be desirable in certain cases and applications. For instance, in case of monitoring of CO and $H_2O$ and $CH_4$ by means of a single optical analyser based upon a diode laser emitting at approximately 2.25 μm, accurate and precise $CH_4$ measurements can be almost impossible to obtain at high range of $CH_4$ concentrations (0-5%), large range of temperature change (296 K-1500 K) and optical beam path lengths of 5 to 40 m. This is because of $CH_4$ absorption lines selected to be close to CO absorption line within a single laser wavelength scan absorb strongly at high CH$_4$ concentrations resulting in almost zero transmission at approximately 2.3 µm.

In such cases different and weaker CH$_4$ absorption lines must be selected such as, for instance, at wavelengths around 1.65 µm. This is outside the scan range of a 2.3 µm tunable diode laser and so a third optical analyser formed by transmitter TR3 and detector D3 operating at a wavelength of 1.65 µm is desirable. This third optical analyser can be added to a dual optical analyser system to result in a triple optical analyser system such as shown in FIG. 6 or 9.

In one particular embodiment that is based on FIG. 6, the first optical analyser formed by transmitter TR1 and detector D1 includes diode laser emitting light at wavelength of approximately 760 nm is used for measurements of O$_2$ and spectral temperature. The second optical analyser formed by transmitter TR2 and detector D2 includes a diode laser emitting at wavelength of approximately 2.3 rpm is used for measurements of CO and H$_2$O. In this embodiment beam splitter 630a has maximum transmission at both 760 nm and 1.65 µm and maximum reflection at approximately 2.3 µm, whilst beam splitter 630b has maximum transmission at wavelengths of 2.3 µm and 1.65 µm and maximum reflection at a wavelength of approximately 760 nm. Beam splitter 630c has maximum transmission at approximately 760 nm and maximum reflection at approximately 1.65 µm, whilst beam splitter 630d has maximum transmission at approximately 2.3 µm and maximum reflection at approximately 1.65 µm. It will be apparent to a skilled person having the benefit of this disclosure that other variations of maximum transmission and maximum reflection for the beam splitters can be used and arranged by changing the location of the transmitters and the detectors with respect to the specific arrangement shown in FIG. 6.

Triple optical analyser measurements can also be necessary in NO$_x$ monitoring, where reporting NH$_3$ and NO concentrations on wet and dry basis is necessary. In such case H$_2$O concentration can be measured at wavelength of 1.39 µm and gas temperature along optical path can be extracted from scanning over two or more H$_2$O absorption lines by means of tuneable diode laser spectroscopy. In another specific embodiment that is based on FIG. 6, the first optical analyser that includes transmitter TR1 and detector D1 performs wavelength modulation absorption spectroscopy using a diode laser emitting at wavelength of approximately 2.25 µm to make measurements of NH$_3$. The second optical analyser that includes transmitter TR2 and detector D2 performs tuneable laser absorption spectroscopy with a quantum cascade laser emitting at wavelength of approximately 5.2 µm to make NO measurements. In this particular embodiment beam splitter 630a has maximum transmission at approximately 1.39 µm and approximately 2.25 µm, and maximum reflection at approximately 5.2 µm, whilst beam splitter 630b has maximum transmission at wavelengths of approximately 1.39 µm and approximately 5.2 µm, and maximum reflection at wavelength of approximately 2.25 µm. Beam splitter 630c has maximum transmission at approximately 2.25 µm and maximum reflection at approximately 1.39 µm, whilst beam splitter 630d has maximum transmission at approximately 5.2 µm and maximum reflection at approximately 1.39 µm.

It will be appreciated that variation of positioning of the transmitters and the detectors from that shown in FIG. 6, including different reflection/transmission specifications for the beam splitters, can be implemented with three optical analysers. One of possible implementation is shown in FIG. 10.

Figure 11:
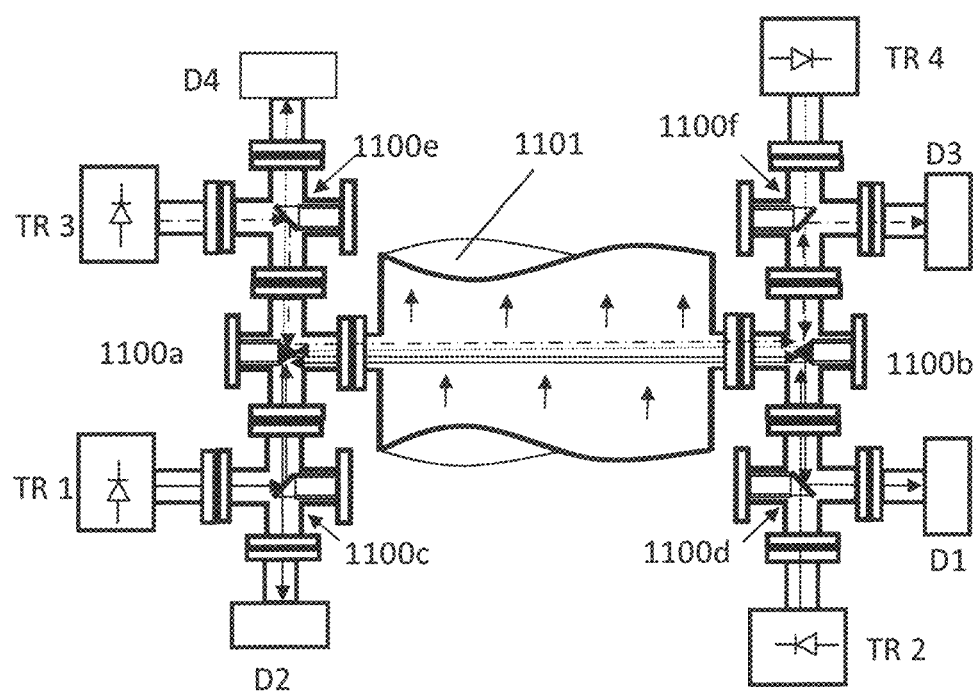
FIG. 11 is a schematic drawing of a tetra optical analyser system according to an embodiment.

It will also be appreciated that embodiments can incorporate any number of optical analyser systems. For example, FIG. 11 shows a tetra optical analyser system incorporating four optical analyser systems. First optical analyser system comprises transmitter TR1 and detector D1 and operates at wavelength λ1. Second optical analyser system comprises transmitter TR2 and detector D2 and operates at wavelength λ2. Third optical analyser system comprises transmitter TR3 and detector D3 and operates at wavelength λ3. Fourth optical analyser system comprises transmitter TR4 and detector D4 and operates at wavelength λ4. In some embodiments, λ1≠λ2≠λ3≠λ4. The tetra optical analyser system of FIG. 11 can thus perform measurements at wavelengths of λ1, λ2, λ3 and λ4. The tetra optical analyser system still only requires two process holes or nozzles in the measurement volume.

The tetra optical analyser system of FIG. 11 can be constructed using six attachment devices 1100a-1100f. Two attachment devices 1100a, 1100b each incorporate a beam splitter as shown in FIG. 8A that are mounted on opposite sides of measurement volume 1101. Attachment devices 1100c, 1100d, 1100e, 1100f each incorporate a beam splitter like beam splitter 550 shown in FIG. 5. Attachment devices 1100c and 1100d each include a dichroic beam splitter reflective at λ1 and transparent at λ2. Attachment devices 1100c and 1100d are mounted on an flange of attachment device 1100a, 1100b, respectively, as shown in FIG. 11. Attachment devices 1100e, 1100f each include a dichroic beam splitter reflective at λ3 and transparent at λ4 and are mounted on a flange of attachment device 1100a, 1100b, respectively, as shown in FIG. 11.

In one particular tetra optical analyser embodiment, the first optical analyser operates at approximately 1.39 m to monitoring H$_2$O and spectral temperature and the second optical analyser operates at approximately 1.592 µm to monitor CO$_2$. The third optical analyser operating at approximately 2.25 µm and the fourth optical analyser operating at approximately 5.2 µm can be used for NH$_3$ and NO measurements.

Figure 12:
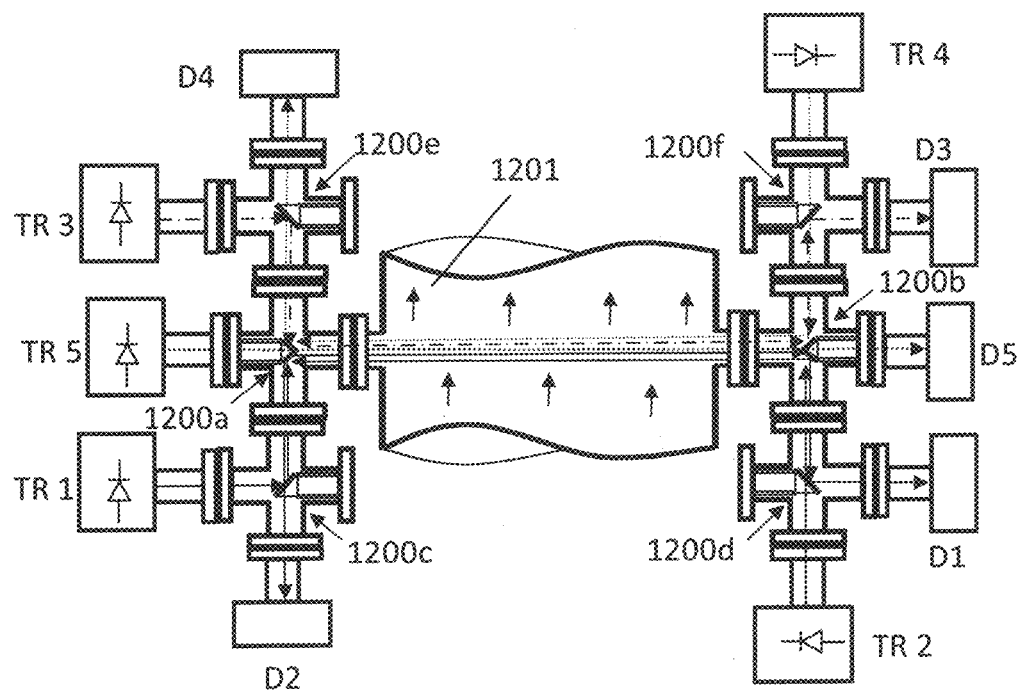
FIG. 12 is a schematic drawing of a penta optical analyser system according to an embodiment.

The tetra optical analyser system shown in FIG. 11 can be further modified to form a penta optical analyser system incorporating five optical analyser systems. This is shown in FIG. 12. First optical analyser system comprises transmitter TR1 and detector D1 and operates at wavelength λ1. Second optical analyser system comprises transmitter TR2 and detector D2 and operates at wavelength λ2. Third optical analyser system comprises transmitter TR3 and detector D3 and operates at wavelength λ3. Fourth optical analyser system comprises transmitter TR4 and detector D4 and operates at wavelength λ4. Fifth optical analyser system comprises transmitter TR5 and detector D5 and operates at wavelength λ5. In some embodiments, λ1≠λ2≠λ3≠λ4≠λ5. The tetra optical analyser system of FIG. 11 can thus perform measurements at wavelengths of λ1, λ2, λ3, λ4 and λ5.

The system of FIG. 11 can be modified to result in the penta optical analyser system of FIG. 12 as described in the following. A dual beam splitter like that shown in FIG. 8B is inserted into each of attachment devices 1200a, 1200b. One of the dichroic windows of each dual beam splitter has a maximum reflectivity at λ1 and λ2, and the other dichroic window of each dual beam splitter has maximum reflectivity at λ3 and λ5. Both dichroic windows of each beam splitter have maximum transmission at λ3.

A fifth transmitter TR5 is attached to an flange of attachment device 1200a, and a fifth detector D5 is attached to a flange of attachment device 1200b. This results in an additional fifth optical analyser emitting at wavelength λ5. The embodiment of FIG. 12 can allow all five optical analysers to probe and measure species along a single beam path through the process in the measurement volume 1201.

In one particular embodiment, beam splitters based upon dual dichroic windows (see FIG. 8B) are used. In this embodiment a beam splitter reflects at approximately 1.39 µm, approximately 1.592 µm and transmits optical radiation at approximately 1.738 µm, to allow $H_2O$ and spectral temperature, $CO_2$ and HCl to be measured by the first, second and fifth optical analysers, respectively. Another beam splitter reflects at approximately 2.25 µm, approximately 5.2 µm and either transmits or absorbs at approximately 1.738 µm, to allow $NH_3$ and NO to be measured by the third and fourth optical analysers. In total, all 5 species ($H_2O$ and spectral temperature, $CO_2$, HCl, $NH_3$ and NO) can be measured along a single optical path. Other combination of the analysers and penta measurements are feasible and will be readily apparent to the skilled person having the benefit of this specification.

It will be appreciated that any of the embodiments described herein can make use of one or more multi-component analysers; that is, individual analysers that are able to detect more than one measurand species. The inventors have determined through experimentation that a transmission of at least 75 to 85%, and a reflectivity of at least 80 to 90%, can be achieved for beam splitters at 90 degrees to the beam axis, so there is no significant loss of optical power due to the use of one or more beam splitters. Transmission and reflectivity are expected to be higher for beam splitters at 45 degrees to the beam axis.

Figure 13B:
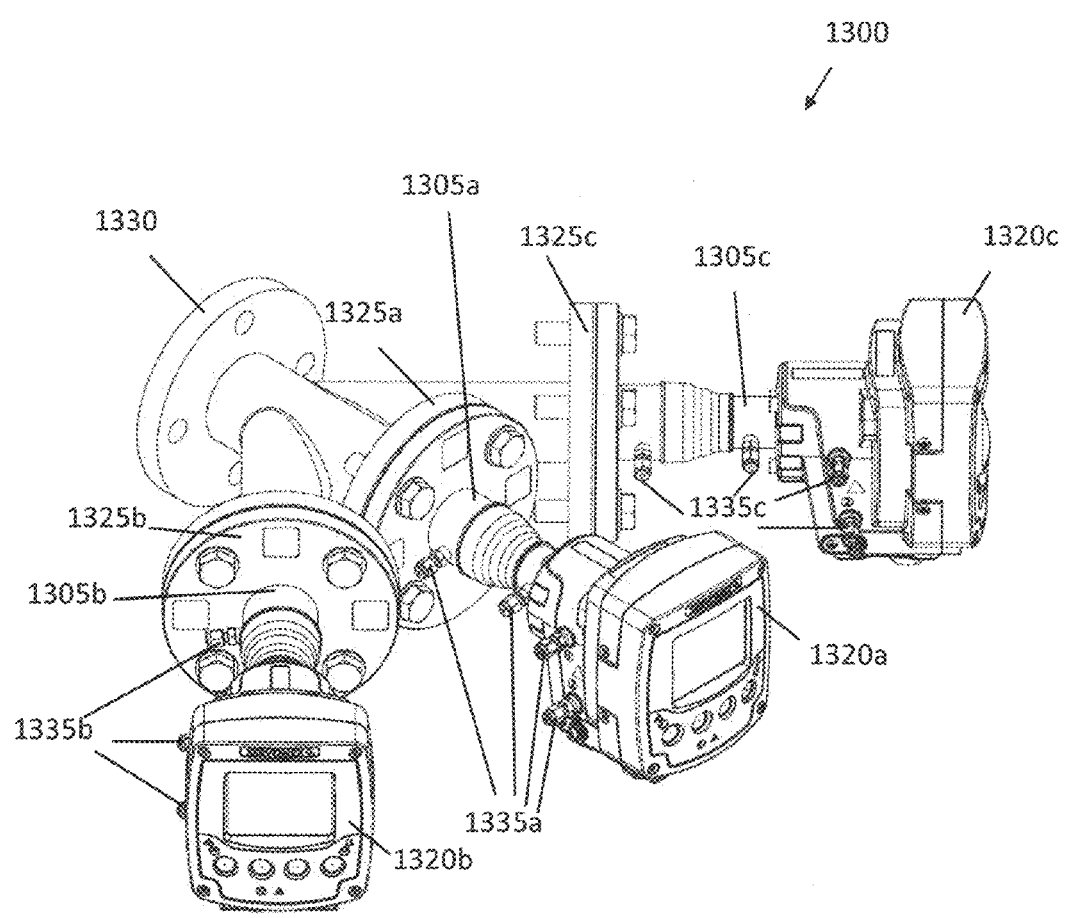
FIG. 13B is a perspective view of the triple beam arrangement shown in FIG. 13A.

FIGS. 13A and 13B show in schematic form an alternative attachment and alignment device 1300 according to another embodiment. Device 1300 includes a central arm 1305*a* and side arms 1305*b* and 1305*c*. The side arms 1305*b* and 1305*c* both join the central arm 1305*a* at a point part way along the length of central arm 1305*a*. Each arm has an interior passage along which a light beam can be directed, thereby forming an optical path that terminates at the distal end of the respective arm. In the illustrated embodiment the beams are shown in truncated form, but it will be appreciated that this is an artefact of the illustration only and that in reality each beam continues into a measurement volume (not shown).

Attachment and alignment device 1300 also includes an alignment assembly 1308. In the illustrated embodiment, alignment assembly 1308 comprises two beam splitters 1310*a*, 1310*b*. In the illustrated embodiment each beam splitter 1310*a*, 1310*b* takes the form of at least one transmissive surface or an aperture and/or at least one reflective surfaces. Alignment assembly 1308 is located in the vicinity of the point at which side arms 1305*b*, 1305*c* join central arm 1305*a* such that the optical path associated with each arm passes through alignment assembly 1308. In particular, the optical path of each side arm passes through a respective one of beam splitters 1310*a*, 1310*b*. This allows a combination of three or more beams (1315*a*, 1315*b*, 1315*c*) to pass through a single aperture into a measurement volume (not shown). The transmissive surface may be a window (or there may simply be an aperture) in the housing. It will be appreciated by the skilled person that, although FIGS. 13A and 13B show three beams, modification such that two beams can be transmitted through either reflective surfaces or a reflective surface and transmissive surface is also possible. It will also be appreciated that the arrangement shown in FIGS. 13A and 13B could also be modified to combine or separate more than three beams.

Advantageously, as is clear from FIG. 13A in particular, the angular input for the beams is not required to be perpendicular to the transmission axis for side arms 1305*b*, 1305*c*. In some instances, the non-perpendicular arrangement may be preferable for mechanical mounting arrangements or for visual display.

The distal end of each arm includes a housing 1320*a*, 1320*b*, 1320*c*, respectively. The housing may house a transmitter, a receiver or a combined transmitter/receiver unit. It will be appreciated than the housing on one arm may house the same unit as is housed on one of the other arms, or it may house a different unit from the one housed on one of the other arms.

Optionally, each arm may include a secondary flange attachment and adjustment device 1325*a*, 1325*b*, 1325*c*. Each secondary flange attachment and adjustment device 1325*a*, 1325*b*, 1325*c* is independently adjustable. This advantageously allows each arm to be adjusted independently of the other arms, for particularly precise beam alignment. Device 1300 is secured in place, e.g. to the wall of a measurement volume, using a suitable securing device. In the illustrated embodiment a flange 1330 is used, but other securing devices known to the skilled person can be used instead.

Each arm preferably includes one or more purge ports 1335*a*, 1335*b*, 1335*c*. These are used as inlets and outlets for purge gas. One or more of the purge ports may be located in the vicinity of housing 1320*a*, 1320*b*, 1320*c*.

It will be appreciated that one or more attachment and alignment devices, like attachment and alignment device 1300, can be used in any one of the arrangements shown in FIGS. 3C, 6, 7, 9, 10, 11 and 12 to provide a single composite beam or a set of closely aligned beams.

Advantages of embodiments described herein include:
i) Quick installation and use of a new optical analyser for measurements of completely different species at different wavelengths using the same mechanical arrangement with only two process holes or nozzles in a measurement volume. Only the beam splitters need to be changed, whilst all the same mechanical arrangement can be used without modification. This has associated cost and time savings.
ii) Each optical analyser system is independent of the other, meaning that in the event of failure of one analyser, measurements by the rest of the optical analyser system are not interrupted whilst the failed optical analyser is repaired.
iii) Embodiments facilitate the quick change or substitution of a failed or obsolete optical analyser with a new or upgraded optical analyser. In the case where the replacing optical analyser operates at the same wavelength as the replaced optical analyser, there is not even a need to substitute any beam splitters when the change is made. This allows for measurement the same or additional species in case of failure of one or more analysers. It is also not necessary to restrict the system to analysers of the same type; instead, the analyser system can include different types of optical analysers that may be, for example, each manufactured by a different company.
iv) Embodiments facilitate easy maintenance or interchange of beam splitters mounted in the attachment devices. For example, in the case of contamination of a beam splitter by e.g. dust, dirt etc., the affected beam splitter can be quickly and easily removed, cleaned and then installed back into original position, or can be replaced with a new beam splitter, without having to dismount and then remount all of the optical analysers. This is a significant time saving.

v) Embodiments facilitate the upgrade of existing dual analyser systems to triple, tetra and penta optical analyser systems that each use only two mounting flanges or nozzles on the measurement volume. This makes it possible to upgrade existing systems to measure multiple species along a single optical path through the measurement volume. The problems associated with optical analysers aligned along different optical paths are avoided.

vi) Embodiments require only a single entrance and exit hole for the measurement volume, and correspondingly require only two nozzles (one for the entrance hole, one for the exit hole). This reduces installation cost and time. A corresponding reduction in the volume of purge gas that the system requires is achieved, again reducing costs.

Whilst the invention has been illustrated in preferred embodiments, it should be readily apparent to someone skilled in the art that the present invention is not limited thereby, but is intended to cover all alternatives, modifications and equivalents that are included within the scope of invention as defined by the following claims. In addition, although this specification has primarily focussed on tunable diode laser absorption applications, it will be understood that embodiments could equally be applied for other optical absorption measurement techniques such as using quantum cascade lasers, inter-band cascade lasers, external cavity laser diodes, external cavity quantum cascade lasers, external cavity inter-band cascade lasers, light emitting diodes or incandescent (black or grey body radiation) sources with appropriate light detectors.

In addition to the embodiments described previously and claimed in the appended claims, the following is a list of additional embodiments, which may serve as the basis for additional claims in this application or subsequent divisional applications.

Embodiment 1

An attachment and alignment device for mounting a plurality of components of an optical analysis system for optical communication with a measurement volume, to enable performance of multiple optical measurements along aligned optical paths through the measurement volume, wherein the device comprises: a first attachment point for attaching the device at a position enabling optical communication with a measurement volume; a mount for mounting an optical alignment device; a plurality of additional attachment points at distinct angular positions relative to the mount, each of the plurality of additional attachment points enabling attachment of: a light source unit; a light detection unit; or a combination unit comprising at least one light source and at least one detector; to provide a distinct optical path between the mount and each of the additional attachment points; and at least one optical alignment device for mounting on the mount, the optical alignment device being configured to provide optical alignment through the measurement volume of light that passes along said distinct optical paths between the mount and each of the additional attachment points.

Embodiment 2

A device according to embodiment 1, wherein the optical alignment results in a single optical path through the measurement volume, or a plurality of closely aligned optical paths through the measurement volume, for light that passes along said distinct optical paths between the mount and each of the additional attachment points.

Embodiment 3

A device according to embodiment 1 or embodiment 2, wherein the at least one optical alignment device comprises at least one beam splitter.

Embodiment 4

A device according to embodiment 3, wherein the mount comprises a mount for a beam splitter or a mount for a beam splitter holder for holding a beam splitter.

Embodiment 5

A device according to embodiment 1, comprising a hollow body defining said distinct optical paths, at least some of which paths are oriented at non-zero angles to each other, and a beam splitter holder for holding a beam splitter to enable light that is incident on the beam splitter to be transmitted along respective ones of said distinct optical paths and along the aligned optical paths through the measurement volume.

Embodiment 6

A device according to embodiment 5, wherein the hollow body is arranged such that at least some of said distinct optical paths are perpendicular with respect to one another.

Embodiment 7

A device according to embodiment 6, wherein the beam splitter is part of an alignment assembly, the assembly comprising a plurality of beam splitters and wherein each beam splitter comprises a transmissive surface or a reflective surface.

Embodiment 8

A device according to embodiment 6 or embodiment 7, wherein the hollow body defines a plurality of arms, each arm associated with one of said distinct optical paths.

Embodiment 9

A device according to embodiment 8, wherein at least one arm includes a secondary flange attachment and adjustment device at an intermediate position along a length of the respective arm, the secondary flange attachment and adjustment device configured to allow the alignment of the optical path associated with the respective arm to be adjusted independently of the other arms.

Embodiment 10

A device according to any one of embodiments 5 to 9, wherein the beam splitter holder is releasably engageable within the device.

Embodiment 11

A device according to embodiment 10, wherein the beam splitter holder, when released, is slidably removable from the device.

Embodiment 12

A device according to any of embodiments 3 to 11, comprising adjustment means to provide adjustment of the beam splitter location and orientation.

Embodiment 13

A device according to embodiment 12, wherein the adjustment means enables the beam splitter to be adjusted to an optimum position using a manual or automated procedure.

Embodiment 14

A device according to embodiment 12, wherein the adjustment means comprises an automated control mechanism for automated movement of the beam splitter to a required position or oscillatory movement about a position.

Embodiment 15

A device according to any of embodiments 3 to 14, wherein the beam splitter is a wavelength-selective beam splitter.

Embodiment 16

A device according to any of embodiments 3 to 14, wherein the beam splitter provides polarisation-dependent selective transmission or reflection of incident light.

Embodiment 17

A device according to any of embodiments 3 to 16, wherein the beam splitter is mounted on a piezoelectric element which is controlled to oscillate around an average position to provide a varying optical path length for light passing through the measurement volume.

Embodiment 18

A device according to any one of embodiments 3 to 17, wherein the beam splitter is a mirror or prism that is movable between a plurality of orientations for selective optical alignment with a subset of the at least two independently connected components.

Embodiment 19

A device according to any one of embodiments 3 to 11 or embodiments 15 to 18, where the beam splitter is mechanically fixed in position.

Embodiment 20

A device according to any one of embodiments 4 to 11, where the beam splitter holder is sealed in place within device.

Embodiment 21

A device according to any one of the embodiments 3 to 20, wherein a beam splitter is removable from the beam splitter holder.

Embodiment 22

A device according to any one of the embodiments 3 to 21, wherein a beam splitter and a beam splitter holder are combined into a single unit.

Embodiment 23

A device according to any one of embodiments 3 to 22, comprising at least one dichroic beam splitter which is based upon a either an optical flat substrate or a wedged window substrate.

Embodiment 24

A device according to any one of embodiments 3 to 22, comprising at least one dichroic beam splitter that is based upon a prism with reflective coatings on both sides.

Embodiment 25

A device according to any one of the preceding embodiments, comprising at least one beam splitter that is a trichroic beam splitter based upon two combined dichroic beam splitters oriented at a predefined angle.

Embodiment 26

A device according to any one of the preceding embodiments, further comprising means to seal and purge an internal volume of the device.

Embodiment 27

A device according to any one of the preceding embodiments, further comprising at least one optical component, such as a window and/or optical pass band filter and/or lens, and means to purge the at least one optical component.

Embodiment 28

A device according to embodiment 27, wherein said device includes means to seal and purge an internal volume of the device and/or means to purge the at least one optical component via a single purge gas input port.

Embodiment 29

A device according to any one of the preceding embodiments, wherein at least one attachment point is provided with a blanking attachment.

Embodiment 30

A device according to embodiment 29, wherein the blanking attachment includes a seal.

Embodiment 31

A device according to any preceding embodiment, wherein the first attachment point is provided with a blanking and sealing attachment for sealing with a window, pass band filter or lens transparent to the wavelengths of interest.

Embodiment 32

A device according to any one of the preceding embodiments, wherein an attachment point is provided with a blanking and sealing attachment for sealing with a diffuser transparent to the wavelengths of interest.

Embodiment 33

A device according to any one of the preceding embodiments, wherein the first attachment point is provided with an adjustable and sealable attachment means that is configured for attaching the device to a wall of the measurement volume.

Embodiment 34

A device according to any one of the preceding embodiments, wherein the plurality of additional attachment points each comprise adjustable attachment means.

Embodiment 35

A device according to embodiment 34, wherein the adjustable attachment means are sealable.

Embodiment 36

A device according to any one of the preceding embodiments, wherein the second and third attachment points incorporate a seal.

Embodiment 37

A device according to any one of the preceding embodiments, including means for sealing the device when a plurality of components are attached to respective ones of the plurality of additional attachment points.

Embodiment 38

A device according to any one of the previous embodiments, comprising a dual beam splitter consisting of two dichroic windows, the first window having maximum reflectivity at one wavelength range, whilst the second window has maximum reflectivity at a second wavelength range, but both windows transmitting in a third wavelength range.

Embodiment 39

A device according to any one of the preceding embodiments, where the device contains a plurality of beam splitters and attachment points.

Embodiment 40

A device according to any preceding embodiment, wherein the light source unit comprises a plurality of light sources.

Embodiment 41

A device according to any preceding embodiment, wherein light detection unit comprises a plurality of detectors.

Embodiment 42

A device according to any preceding embodiment, wherein the plurality of additional attachment points each comprise a flange with means for mechanical attachment.

Embodiment 43

A device according to any preceding embodiment, wherein the first attachment point is adapted for attachment to a wall mount, which wall mount provides optical alignment with said optical path through the measurement volume.

Embodiment 44

A device according to any preceding embodiment, wherein the first attachment point comprises a sealing means for achieving a fluid-tight sealed connection to a side wall of the measurement volume.

Embodiment 45

A device according to any preceding embodiment, further comprising at least one sealable or purgeable reference cell that is configured to provide a reference absorption signal.

Embodiment 46

A device according to embodiment 45, wherein the device further comprises a manual assembly or a motorised assembly that is configured to move the reference cell.

Embodiment 47

A system composed of at least two devices according to any of the preceding embodiments, whereby the mounting and optical alignment of a plurality of components of an optical analysis system is achieved by mounting the at least two devices to the side of a measurement volume such that at least one of the devices is not in direct optical alignment with the optical path through the measurement volume, but optical alignment is achieved by reflective means.

Embodiment 48

A modular optical analysis system comprising: at least one attachment and alignment device according to any one of embodiments 1 to 46; and at least two units, each of which comprises a light source unit, a light detector unit or a combination unit that comprises at least one light source and at least one detector.

Embodiment 49

The system of embodiment 48, comprising first and second attachment and alignment devices each according to any one of embodiments 1 to 46, wherein the first and second attachment and alignment devices are sealed together and wherein the internal volume of the system comprises a measurement cell volume.

Embodiment 50

The system of embodiment 49, further comprising at least one intermediate measurement cell located between the first and second attachment and alignment devices.

Embodiment 51

A device for attaching a plurality of optical components to a side of a measurement volume, comprising: a hollow body defining a plurality of partial optical pathways; a plurality of flanges at ends of the partial optical pathways; and at least one beam splitter or beam splitter holder that is releasably held in the hollow body portion.

Embodiment 52

A device according to embodiment 51, wherein the plurality of flanges comprises: a first flange for connection to a side wall of the measurement volume; and at least two flanges for connection of any two units, each of which units comprises a light source unit, a light detection unit or a combination unit that comprises at least one light source and at least one detector.

Embodiment 53

A device according to embodiment 52, wherein the first flange comprises a sealing means for achieving a fluid-tight sealed connection to a side wall of the measurement volume.

The invention claimed is:

1. An attachment and alignment device for mounting a plurality of components of an optical analysis system for optical communication with a measurement volume, to enable performance of multiple optical measurements along aligned optical paths through the measurement volume, wherein the device comprises:
    a first connector attachment for attaching the device at a position enabling optical communication with a measurement volume;
    a carriage configured to mount an optical alignment device;
    a plurality of additional connector attachments at distinct angular positions relative to the carriage, each of the plurality of additional connector attachments enabling attachment and detachment of: a light source unit; a light detection unit; or a combination unit comprising at least one light source and at least one detector; to provide a distinct optical path between the carriage and each of the additional connector attachments: and
    at least one optical alignment device for mounting on the carriage, the optical alignment device being configured to provide optical alignment through the measurement volume of light that passes along said distinct optical paths between the mount carriage and each of the additional connector attachment.

2. A device according to claim 1, wherein the optical alignment results in a single optical path through the measurement volume, or a plurality of closely aligned optical paths through the measurement volume, for light that passes along said distinct optical paths between the carriage and each of the additional connector attachment.

3. A device according to claim 1, wherein the at least one optical alignment device comprises at least one beam splitter.

4. A device according to claim 3, comprising an adjustment device, wherein the adjustment device enables the beam splitter to be adjusted to an optimum position using a manual or automated procedure.

5. A device according to claim 4, wherein the adjustment device comprises an automated control mechanism for automated movement of the beam splitter to a required position or oscillatory movement about a position.

6. A device according to claim 3, wherein the beam splitter is a wavelength-selective beam splitter.

7. A device according to claim 3, wherein the beam splitter provides polarisation-dependent selective transmission or reflection of incident light.

8. A device according to claim 3, wherein the beam splitter is mounted on a piezoelectric element.

9. A device according to claim 3, wherein the beam splitter is a mirror or prism that is movable between a plurality of orientations for selective optical alignment with a subset of the at least two independently connected components.

10. A device according to claim 3, comprising one of:
    at least one dichroic beam splitter which is based upon a either an optical flat substrate or a wedged window substrate; or
    at least one dichroic beam splitter that is based upon a prism with reflective coatings on both sides; or
    at least one beam splitter that is a trichroic beam splitter based upon two combined dichroic beam splitters oriented at a predefined angle.

11. A device according to claim 1, comprising a hollow body defining said distinct optical paths, at least some of which paths are oriented at non-zero angles to each other, and a beam splitter holder for holding a beam splitter to enable light that is incident on the beam splitter to be transmitted along respective ones of said distinct optical paths and along the aligned optical paths through the measurement volume.

12. A device according to claim 11, wherein the hollow body is arranged such that at least some of said distinct optical paths are not perpendicular with respect to one another.

13. A device according to claim 12, wherein the beam splitter is part of an alignment assembly, the assembly comprising a plurality of beam splitters and wherein each beam splitter comprises a transmissive surface or a reflective surface.

14. A device according to claim 12, wherein the hollow body defines a plurality of arms, each arm associated with one of said distinct optical paths.

15. A device according to claim 14, wherein at least one arm includes a secondary flange attachment and adjustment device at an intermediate position along a length of the respective arm, the secondary flange attachment and adjustment device configured to allow the alignment of the optical path associated with the respective arm to be adjusted independently of the other arms.

16. A device according to claim 11, wherein the beam splitter holder is releasably engageable within the device.

17. A device according to claim 1, further comprising at least one optical component, such as a window and/or optical pass band filter and/or lens, and a purging device configured to purge the at least one optical component.

18. A device according to claim 17, wherein said device includes a purging and sealing device configured to:
    seal and purge an internal volume of the device; and/or
    purge the at least one optical component via a single purge gas input port.

19. A device according to claim 1, wherein at least one attachment point is provided with a blanking attachment.

20. A device according to claim 19, wherein the blanking attachment includes a seal.

21. A device according to claim 1, wherein the plurality of additional connector attachments are each adjustable.

22. A device according to claim 1, wherein the plurality of additional connector attachments are each adjustable and sealable.

23. A device according to claim 1, comprising a dual beam splitter consisting of two dichroic windows, the first window having maximum reflectivity at one wavelength range, whilst the second window has maximum reflectivity at a second wavelength range, but both windows transmitting in a third wavelength range.

24. A device according to claim 1, wherein the plurality of additional connector attachments each comprise a flange with an attachment device configured to allow a light source, light detector or combined light source and detector to be mechanically attached to and detached from the attachment point.

25. A device according to claim 1, further comprising at least one sealable or purgeable reference cell that is configured to provide a reference absorption signal.

26. A device according to claim 25, wherein the device further comprises a manual assembly or a motorised assembly that is configured to move the reference cell.

27. A system composed of at least two devices according to claim 1, whereby the mounting and optical alignment of a plurality of components of an optical analysis system is achieved by mounting the at least two devices to the side of a measurement volume such that at least one of the devices is not in direct optical alignment with the optical path through the measurement volume, but optical alignment is achieved by a reflective element.

28. A modular optical analysis system comprising:
at least one attachment and alignment device according to claim 1; and
at least two units for attachment at selected ones of the plurality of additional connector attachments, each of which units comprises a light source unit, a light detector unit or a combination unit that comprises at least one light source and at least one detector.

29. The system of claim 28, comprising first and second attachment and alignment devices each according to claim 1, wherein the first and second attachment and alignment devices are sealed together and wherein the internal volume of the system comprises a measurement cell volume.

30. The system of claim 29, further comprising at least one intermediate measurement cell located between the first and second attachment and alignment devices.

31. A device according to claim 1, wherein the first connector attachment and the additional connector attachments are each selected from the group consisting of flanges, threaded portions and adjustable attachment mechanisms.

* * * * *